United States Patent
Qiu et al.

(10) Patent No.: US 11,548,884 B2
(45) Date of Patent: Jan. 10, 2023

(54) CYCLIC AMIDINE COMPOUNDS FOR THE TREATMENT OF AUTOIMMUNE DISEASE

(71) Applicant: Hoffmann-La Roche Inc., Little Falls, NJ (US)

(72) Inventors: Zongxing Qiu, Shanghai (CN); Hong Shen, Shanghai (CN); Wei Zhu, Shanghai (CN); Fabian Dey, Basel (CH); Ge Zou, Shanghai (CN); Hongtao Xu, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 17/274,040

(22) PCT Filed: Sep. 6, 2018

(86) PCT No.: PCT/EP2018/073920
§ 371 (c)(1),
(2) Date: Mar. 5, 2021

(87) PCT Pub. No.: WO2020/048595
PCT Pub. Date: Mar. 12, 2020

(65) Prior Publication Data
US 2021/0340134 A1    Nov. 4, 2021

(51) Int. Cl.
*C07D 413/14* (2006.01)
*C07D 211/70* (2006.01)
*C07D 487/10* (2006.01)

(52) U.S. Cl.
CPC .......... *C07D 413/14* (2013.01); *C07D 211/70* (2013.01); *C07D 487/10* (2013.01)

(58) Field of Classification Search
CPC .. C07D 413/14; C07D 211/70; C07D 487/10; A61K 31/517; A61K 31/551
See application file for complete search history.

(56) References Cited

U.S. PATENT DOCUMENTS

| | | |
|---|---|---|
| 2015/0105370 A1 | 4/2015 | Carlson et al. |
| 2017/0174653 A1* | 6/2017 | Sherer .................... A61P 25/00 |
| 2018/0037570 A1 | 8/2018 | Sherer et al. |
| 2019/0185469 A1 | 6/2019 | Dyckman et al. |
| 2021/0253575 A1 | 8/2021 | Dey et al. |
| 2021/0269451 A1 | 9/2021 | Liu et al. |
| 2021/0300924 A1 | 9/2021 | Liu et al. |
| 2021/0300947 A1 | 9/2021 | Dey et al. |
| 2021/0323977 A1 | 10/2021 | Liu et al. |
| 2021/0340136 A1 | 11/2021 | Zhu et al. |
| 2021/0355122 A1 | 11/2021 | Dey et al. |
| 2021/0395239 A1 | 12/2021 | Dey et al. |

FOREIGN PATENT DOCUMENTS

| | | |
|---|---|---|
| EP | 3623369 A1 | 3/2020 |
| WO | 2015/057655 A1 | 4/2015 |
| WO | 2015/057659 A1 | 4/2015 |
| WO | 2019/028302 A1 | 2/2017 |
| WO | 2017/106607 A1 | 6/2017 |
| WO | 2018/005586 A1 | 1/2018 |
| WO | 2018/026620 A1 | 2/2018 |
| WO | 2018/031434 A1 | 2/2018 |
| WO | 2018/047081 A1 | 3/2018 |
| WO | 2018/049089 A1 | 3/2018 |
| WO | 2019/018354 A1 | 1/2019 |
| WO | 2019/028301 A1 | 2/2019 |
| WO | 2019/099336 A1 | 5/2019 |
| WO | 2019/118799 A1 | 6/2019 |
| WO | 2019/123294 A2 | 6/2019 |
| WO | 2019/125849 A1 | 6/2019 |
| WO | 2019/126081 A1 | 6/2019 |
| WO | 2019/126082 A1 | 6/2019 |
| WO | 2019/126083 A1 | 6/2019 |
| WO | 2019/126113 A1 | 6/2019 |
| WO | 2019/126242 A1 | 6/2019 |
| WO | 2019/126253 A1 | 6/2019 |
| WO | 2019/220390 A1 | 11/2019 |

OTHER PUBLICATIONS

Choi et al., Preventing the development of SLE: identifying risk factors and proposing pathways for clinical care, Lupus (2016) 25, pp. 838-849.*

(Continued)

*Primary Examiner* — Deepak R Rao
(74) *Attorney, Agent, or Firm* — Katherine J. Mackenzie

(57) ABSTRACT

The present invention relates to compounds of formula (I), wherein $R^1$, $R^2$ and $R^3$ are as described herein, and their pharmaceutically acceptable salt, enantiomer or diastereomer thereof, and compositions including the compounds and methods of using the compounds as antagonist of TLR7 and/or TLR8 and/or TLR9 in the treatment of autoimmune diseases as well as auto-inflammation diseases.

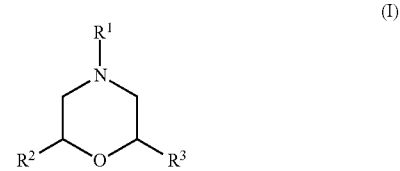

(I)

12 Claims, No Drawings

(56) References Cited

OTHER PUBLICATIONS

Alper, P., et al., "Discovery of potent, orally bioavailable in vivo efficacious antagonists of the TLR7/8 pathway" Bioorg Med Chem Lett 30(17):127366 (1-5) (Sep. 1, 2020).

Knoepfel, T., et al., "Target-Based Identification and Optimization of 5-Indazol-5-yl Pyridones as Toll-like Receptor 7 and 8 Antagonists Using a Biochemical TLR8 Antagonist Competition Assay" J Med Chem 63(15):8276-8295 (Jul. 30, 2020).

Mussari et al., "Discovery of Potent and Orally Bioavailable Small Molecule Antagonists of Toll-like Receptors 7/8/9 (TLR7/8/9)" ACS Med. Chem. Lett. 11:1751-1758 ( 2020).

"International Preliminary Report on Patentability—PCT/EP2018/073920" (dated Mar. 9, 2021, Chapter I), :pps. 1-7 (Mar. 18, 2021).

"International Search Report—PCT/EP2018/073920" (w/Written Opinion), :pps. 1-12 (dated Nov. 15, 2018).

USPTO, "U.S. Appl. No. 17/641,894, filed Mar. 10, 2020 entitled: 'Quinoline Compounds for the Treatment of Autoimmune Disease'".

USPTO, "U.S. Appl. No. 17/756,221, filed May 19, 2022 entitled 'Spiro(isobenzofuranazetidine) Compounds for the Treatment of Autoimmune Disease'".

\* cited by examiner

CYCLIC AMIDINE COMPOUNDS FOR THE TREATMENT OF AUTOIMMUNE DISEASE

The present invention relates to organic compounds useful for therapy and/or prophylaxis in a mammal, and in particular to antagonist of TLR7 and/or TLR8 and/or TLR9 useful for treating systemic lupus erythematosus or lupus nephritis.

FIELD OF THE INVENTION

Autoimmune connective tissue disease (CTD) include prototypical autoimmune syndromes such as Systemic Lupus Erythematosus (SLE), primary Sjögren's syndrome (pSjS), mixed connective tissue disease (MCTD), Dermatomyositis/Polymyositis (DM/PM), Rheumatoid Arthritis (RA), and systemic sclerosis (SSc). With the exception of RA, no really effective and safe therapies are available to patients. SLE represents the prototypical CTD with a prevalence of 20-150 per 100,000 and causes broad inflammation and tissue damage in distinct organs, from commonly observed symptoms in the skin and joints to renal, lung, or heart failure. Traditionally, SLE has been treated with non-specific anti-inflammatory or immunosuppressive drugs. However, long term usage of immunosuppressive drug, e.g. corticosteroids is only partially effective, and is associated with undesirable toxicity and side effects. Belimumab is the only FDA-approved drug for lupus in the last 50 years, despite its modest and delayed efficacy in only a fraction of SLE patients (Navarra, S. V. et al *Lancet* 2011, 377, 721.). Other biologics, such as anti-CD20 mAbs, mAbs against or soluble receptors of specific cytokines, have failed in most clinical studies. Thus, novel therapies are required that provide sustained improvement in a greater proportion of patient groups and are safer for chronic use in many autoimmune as well as auto-inflammation diseases.

Toll Like Receptors (TLR) are an important family of pattern recognition receptors (PRR) which can initiate broad immune responses in a wide variety of immune cells. As natural host defense sensors, endosomal TLRs 7, 8 and 9 recognize nucleic acids derived from viruses, bacteria; specifically, TLR7/8 and TLR9 recognize single-stranded RNA (ssRNA) and single-stranded CpG-DNA, respectively. However, aberrant nucleic acid sensing of TRL7,8,9 is considered as a key node in a broad of autoimmune and auto-inflammatory diseases (Krieg, A. M. et al. *Immunol. Rev.* 2007, 220, 251. Jiménez-Dalmaroni, M. J. et al *Autoimmun Rev.* 2016, 15, 1. Chen, J. Q., et al. *Clinical Reviews in Allergy & Immunology* 2016, 50, 1.) Therefore, TLR7,8,9 represents a new therapeutic target for autoimmune and auto-inflammatory diseases, for which no effective steroid-free and non-cytotoxic oral drugs exist, and inhibition of these pathways from the very upstream may deliver satisfying therapeutic effects. From a safety perspective, because there are multiple nucleic acid sensing pathways (e.g. other TLRs, cGAS/STING), such redundancy should still allow responses to infection in the presence of TLR789 inhibition. As such, we proposed and invented oral compounds that target and suppress TLR7,8,9 for the treatment of autoimmune and auto-inflammatory diseases.

SUMMARY OF THE INVENTION

The present invention relates to novel compounds of formula (I),

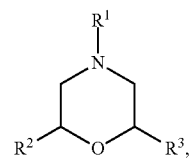

wherein
$R^1$ is

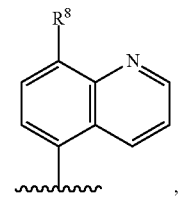

wherein $R^8$ is cyano, $C_{1-6}$alkyl, halogen, halo$C_{1-6}$alkyl or nitro;
$R^2$ is $C_{1-6}$alkyl, $C_{3-7}$cycloalkyl or halo$C_{1-6}$alkyl;
$R^3$ is

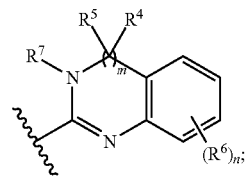

wherein
$R^4$ and $R^5$ are independently selected from H and $C_{1-6}$alkyl;
$R^6$ is H, halogen, $C_{1-6}$alkyl or heterocyclyl;
$R^7$ is H or $C_{1-6}$alkyl;
m is 0, 1, 2 or 3;
n is 1, 2 or 3;
or a pharmaceutically acceptable salt, enantiomer or diastereomer thereof.

Another object of the present invention is related to novel compounds of formula (I), their manufacture, medicaments based on a compound in accordance with the invention and their production as well as the use of compounds of formula (I) as TLR7 and/or TLR8 and/or TLR9 antagonist, and for the treatment or prophylaxis of systemic lupus erythematosus or lupus nephritis. The compounds of formula (I) show superior TLR7 and/or TLR8 and/or TLR9 antagonism activity. In addition, the compounds of formula (I) also show good cytotoxicity, solubility, human microsome stability and SDPK profiles, as well as low CYP inhibition.

DETAILED DESCRIPTION OF THE INVENTION

Definitions
The term "$C_{1-6}$alkyl" denotes a saturated, linear or branched chain alkyl group containing 1 to 6, particularly 1 to 4 carbon atoms, for example methyl, ethyl, n-propyl, isopropyl, n-butyl, isobutyl, tert-butyl and the like. Particular "$C_{1-6}$alkyl" groups are methyl, ethyl and n-propyl.

The term "halogen" and "halo" are used interchangeably herein and denote fluoro, chloro, bromo, or iodo.

The term "haloC$_{1-6}$alkyl" denotes an alkyl group wherein at least one of the hydrogen atoms of the alkyl group has been replaced by same or different halogen atoms, particularly fluoro atoms. Examples of haloC$_{1-6}$alkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, difluoromethyl, trifluoromethyl and trifluoroethyl.

The term "heterocyclyl" denotes a monovalent saturated or partly unsaturated mono- or bicyclic ring system of 3 to 12 ring atoms, comprising 1, 2, or 3 ring heteroatoms selected from N, O and S, the remaining ring atoms being carbon. In particular embodiments, heterocyclyl is a monovalent saturated monocyclic ring system of 4 to 10 ring atoms, comprising 1, 2, or 3 ring heteroatoms selected from N, O and S, the remaining ring atoms being carbon. Examples for monocyclic saturated heterocyclyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, oxazepanyl, diazepanyl, homopiperazinyl, or oxazepanyl. Examples for bicyclic saturated heterocyclyl are aminoazabicyclo[3.2.1]octanyl, aminoazabicyclo[3.2.1]octanyl, C$_{1-6}$alkyldiazaspiro[5.5]undecanyl, diazaspiro[3.5]nonanyl, diazaspiro[4.5]decanyl, diazaspiro[4.5]decanyl, diazaspiro[4.4]nonanyl, diazaspiro[5.5]undecanyl and diazaspiro[5.5]undecanyl. Examples for partly unsaturated heterocyclyl are dihydrofuryl, imidazolinyl, dihydro-oxazolyl, tetrahydropyridinyl, and dihydropyranyl. Monocyclic or bicyclic heterocyclyl can be further substituted by halogen, hydroxy, amino, C$_{1-6}$alkyl, haloC$_{1-6}$alkyl or heterocyclyl.

It is understood that the group with structure as

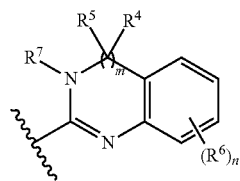

will be equal to

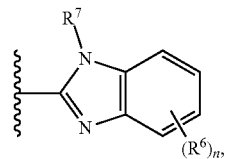

when m is 0.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

The term "A pharmaceutically active metabolite" denotes a pharmacologically active product produced through metabolism in the body of a specified compound or salt thereof. After entry into the body, most drugs are substrates for chemical reactions that may change their physical properties and biologic effects. These metabolic conversions, which usually affect the polarity of the compounds of the invention, alter the way in which drugs are distributed in and excreted from the body. However, in some cases, metabolism of a drug is required for therapeutic effect.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "pharmaceutical composition" denotes a mixture or solution comprising a therapeutically effective amount of an active pharmaceutical ingredient together with pharmaceutically acceptable excipients to be administered to a mammal, e.g., a human in need thereof.

Antagonist of TLR7 and/or TLR8 and/or TLR9

The present invention relates to a compound of formula (I),

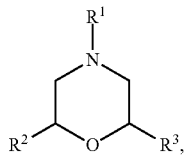

(I)

wherein
R¹ is

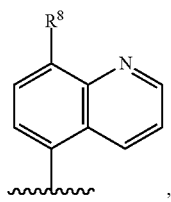

wherein R⁸ is cyano, $C_{1-6}$alkyl, halogen, halo$C_{1-6}$alkyl or nitro;
R² is $C_{1-6}$alkyl, $C_{3-7}$cycloalkyl or halo$C_{1-6}$alkyl;
R³ is

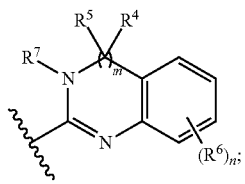

wherein
R⁴ and R⁵ are independently selected from H and $C_{1-6}$alkyl;
R⁶ is H, halogen, $C_{1-6}$alkyl or heterocyclyl;
R⁷ is H or $C_{1-6}$alkyl;
m is 0, 1, 2 or 3;
n is 1, 2 or 3;
or a pharmaceutically acceptable salt, enantiomer or diastereomer thereof.

A further embodiment of present invention is (ii) a compound of formula (I), wherein
R¹ is

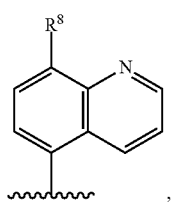

wherein R⁸ is cyano;
R² is $C_{1-6}$alkyl;

R³ is

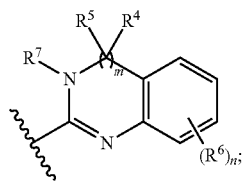

wherein
R⁴ is H;
R⁵ is H;
R⁶ is H, halogen, tetrahydropyridinyl, diazaspiro[4.4]nonanyl, hydroxypiperidinyl, $C_{1-6}$alkylpiperazinyl, morpholinyl, piperazinyl or piperidinyl;
R⁷ is H;
m is 1 or 2;
n is 1, 2 or 3;
or a pharmaceutically acceptable salt, enantiomer or diastereomer thereof.

A further embodiment of present invention is (iii) a compound of formula (I) according to (ii), wherein
R¹ is

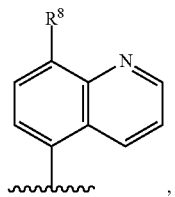

wherein R⁸ is cyano;
R² is methyl;
R³ is

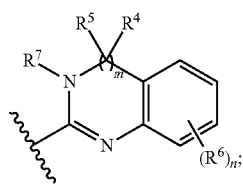

wherein
R⁴ is H;
R⁵ is H;
R⁶ is H, bromo, tetrahydropyridinyl, 2,7-diazaspiro[4.4]nonan-2-yl, hydroxypiperidinyl, methylpiperazinyl, morpholinyl, piperazinyl or piperidinyl;
R⁷ is H;
m is 1 or 2;
n is 1, 2 or 3;
or a pharmaceutically acceptable salt, enantiomer or diastereomer thereof.

A further embodiment of present invention is (iv) a compound of formula (I) according to (ii), wherein R⁶ is $C_{1-6}$alkylpiperazinyl or piperazinyl.

A further embodiment of present invention is (v) a compound of formula (I) according to (iv), wherein R⁶ is methylpiperazinyl or piperazinyl.

A further embodiment of present invention is (vi) a compound of formula (I) according to (iv) or (v), wherein n is 1.

Another embodiment of present invention is that (vii) particular compounds of formula (I) are the following:

5-[(2R,6R)-2-(5-bromo-3,4-dihydroquinazolin-2-yl)-6-methyl-morpholin-4-yl]quinoline-8-carbonitrile;

5-[(2R,6R)-2-(6-bromo-3,4-dihydroquinazolin-2-yl)-6-methyl-morpholin-4-yl]quinoline-8-carbonitrile;

5-[(2R,6R)-2-(1,4-dihydroquinazolin-2-yl)-6-methyl-morpholin-4-yl]quinoline-8-carbonitrile;

5-[(2R,6R)-2-(7-bromo-3,4-dihydroquinazolin-2-yl)-6-methyl-morpholin-4-yl]quinoline-8-carbonitrile;

5-[(2R,6R)-2-(8-bromo-3,4-dihydroquinazolin-2-yl)-6-methyl-morpholin-4-yl]quinoline-8-carbonitrile;

5-[(2R,6R)-2-methyl-6-(5-piperazin-1-yl-3,4-dihydroquinazolin-2-yl)morpholin-4-yl]quinoline-8-carbonitrile;

5-[(2R,6R)-2-methyl-6-(6-piperazin-1-yl-3,4-dihydroquinazolin-2-yl)morpholin-4-yl]quinoline-8-carbonitrile;

5-[(2R,6R)-2-methyl-6-(7-piperazin-1-yl-3,4-dihydroquinazolin-2-yl)morpholin-4-yl]quinoline-8-carbonitrile;

5-[(2R,6R)-2-methyl-6-(8-piperazin-1-yl-3,4-dihydroquinazolin-2-yl)morpholin-4-yl]quinoline-8-carbonitrile;

5-[(2R,6R)-2-[5-(4-hydroxy-1-piperidyl)-3,4-dihydroquinazolin-2-yl]-6-methyl-morpholin-4-yl]quinoline-8-carbonitrile;

5-[(2R,6R)-2-methyl-6-(5-morpholino-3,4-dihydroquinazolin-2-yl)morpholin-4-yl]quinoline-8-carbonitrile;

5-[(2R,6R)-2-methyl-6-[5-(4-methylpiperazin-1-yl)-3,4-dihydroquinazolin-2-yl]morpholin-4-yl]quinoline-8-carbonitrile;

5-[(2R,6R)-2-[5-(2,7-diazaspiro[4.4]nonan-2-yl)-3,4-dihydroquinazolin-2-yl]-6-methyl-morpholin-4-yl]quinoline-8-carbonitrile;

5-[(2R,6R)-2-(6-bromo-4,5-dihydro-3H-1,3-benzodiazepin-2-yl)-6-methyl-morpholin-4-yl]quinoline-8-carbonitrile, 5-[(2R,6R)-2-(4,5-dihydro-3H-1,3-benzodiazepin-2-yl-6-methyl-morpholin-4-yl]quinoline-8-carbonitrile;

5-[(2R,6R)-2-methyl-6-[6-(1,2,3,6-tetrahydropyridin-4-yl)-4,5-dihydro-3H-1,3-benzodiazepin-2-yl]morpholin-4-yl]quinoline-8-carbonitrile;

5-[(2R,6R)-2-methyl-6-(7-piperazin-1-yl-4,5-dihydro-3H-1,3-benzodiazepin-2-yl)morpholin-4-yl]quinoline-8-carbonitrile; and 5-[(2R,6R)-2-methyl-6-[5-(4-piperidyl)-3,4-dihydroquinazolin-2-yl]morpholin-4-yl]quinoline-8-carbonitrile;

or a pharmaceutically acceptable salt, enantiomer or diastereomer thereof.

Synthesis

The compounds of the present invention can be prepared by any conventional means. Suitable processes for synthesizing these compounds as well as their starting materials are provided in the schemes below and in the examples. All substituents, in particular, $R^1$ to $R^8$ are as defined above unless otherwise indicated. Furthermore, and unless explicitly otherwise stated, all reactions, reaction conditions, abbreviations and symbols have the meanings well known to a person of ordinary skill in organic chemistry.

A general synthetic route for preparing the compound of formula (I) is shown in Scheme 1 below.

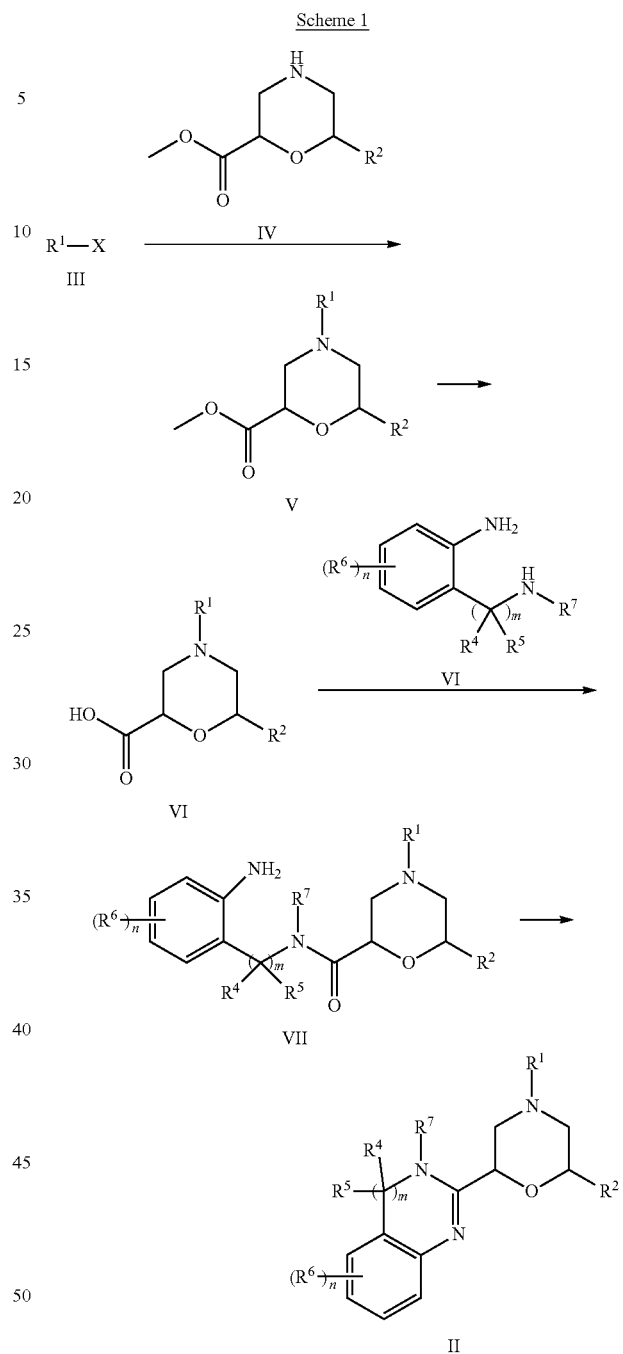

Scheme 1 wherein X is halogen; m is 0, 1, 2 or 3; n is 1, 2 or 3.

The coupling of halide (III) with compound of formula (IV) can be achieved in the presence of a base, such as DIPEA or $K_2CO_3$, or under Buchwald-Hartwig amination conditions (ref: *Acc. Chem. Res.* 1998, 31, 805-818; *Chem. Rev.* 2016, 116, 12564-12649; *Topics in Current Chemistry*, 2002, 219, 131-209; and references cited therein) with a catalyst, such as Ruphos Pd-G2, and a base, such as $Cs_2CO_3$, to provide compound of formula (V). Hydrolysis of compound of formula (V) under basic condition, such as lithium hydroxide in THF and water, gives carboxylate acid (VI), which is coupled with compound of formula (VI) in the presence of a coupling reagent, such as HATU, to give the compound of formula (VII). Under acidic condition, such as HCl in t-BuOH, compound of formula (VII) can be cyclized to afford formula (II). In some embodiment, the compound of formula (VII) may containing a protecting group, e.g. Boc, which will be removed before affording the final compound of formula (II).

This invention also relates to a process for the preparation of a compound of formula (I) comprising any of the following steps:

a) cyclization of compound of formula (VII),

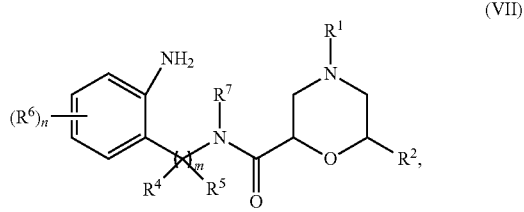

in the presence of an acid;

wherein $R^1$, $R^2$, $R^4$, $R^4$, $R^5$, $R^6$, $R^7$, m and n are defined above.

In step a), the acid can be for example HCl in t-BuOH.

A compound of formula (I) or (II) when manufactured according to the above process is also an object of the invention.

Compounds of this invention can be obtained as mixtures of diastereomers or enantiomers, which can be separated by methods well known in the art, e.g. (chiral) HPLC or SFC.

Indications and Methods of Treatment

The present invention provides compounds that can be used as TLR7 and/or TLR8 and/or TLR9 antagonist, which inhibits pathway activation through TLR7 and/or TLR8 and/or TLR9 as well as respective downstream biological events including, but not limited to, innate and adaptive immune responses mediated through the production of all types of cytokines and all forms of auto-antibodies. Accordingly, the compounds of the invention are useful for blocking TLR7 and/or TLR8 and/or TLR9 in all types of cells that express such receptor(s) including, but not limited to, plasmacytoid dendritic cell, B cell, T cell, macrophage, monocyte, neutrophil, keratinocyte, epithelial cell. As such, the compounds can be used as a therapeutic or prophylactic agent for systemic lupus erythematosus and lupus nephritis.

The present invention provides methods for treatment or prophylaxis of systemic lupus erythematosus and lupus nephritis in a patient in need thereof.

Another embodiment includes a method of treating or preventing systemic lupus erythematosus and lupus nephritis in a mammal in need of such treatment, wherein the method comprises administering to said mammal a therapeutically effective amount of a compound of formula (I), a stereoisomer, tautomer, prodrug or pharmaceutically acceptable salt thereof.

EXAMPLES

The invention will be more fully understood by reference to the following examples. They should not, however, be construed as limiting the scope of the invention.

Abbreviations

The invention will be more fully understood by reference to the following examples. They should not, however, be construed as limiting the scope of the invention.

Abbreviations used herein are as follows:

| | |
|---|---|
| ACN: | acetonitrile |
| Boc$_2$O: | di-tert-butyl dicarbonate |
| Tf$_2$O: | triflic anhydride |
| DCM: | dichloromethane |
| DDI | drug-drug-interaction |
| DIPEA | diethylisopropylamine |
| DMA | dimethylacetamide |
| EA or EtOAc: | ethyl acetate |
| FA: | formic acid |
| HATU | 1-[Bis(dimethylamino)methylene]-1H-1,2,3-triazolo[4,5-b]pyridinium 3-oxid hexafluorophosphate |
| HLM | human liver microsome |
| hr | hour |
| hrs | hours |
| IC$_{50}$: | half inhibition concentration |
| LCMS | liquid chromatography-mass spectrometry |
| LYSA | lyophilisation solubility assay |
| MS: | mass spectrometry |
| PE: | petroleum ether |
| prep-HPLC: | preparative high performance liquid chromatography |
| rt: | rt |
| RT: | retention time |
| RuPhos Pd G2: | chloro(2-dicyclohexylphosphino-2',6'-diisopropoxy-1,1'-biphenyl)[2-(2'-amino-1,1'-biphenyl)]palladium(II) 2nd generation |
| SFC: | supercritical fluid chromatography |
| TFA: | trifluoroacetic acid |
| v/v | volume ratio |

General Experimental Conditions

Intermediates and final compounds were purified by flash chromatography using one of the following instruments: i) Biotage SP1 system and the Quad 12/25 Cartridge module. ii) ISCO combi-flash chromatography instrument. Silica gel brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using XBridge™ Prep-C18 (5 μm, OBD™ 30×100 mm) column, SunFire™ Prep-C18 (5 μm, OBD™ 30×100 mm) column, Phenomenex Synergi-C18 (10 μm, 25×150 mm) or Phenomenex Gemini-C18 (10 μm, 25×150 mm). Waters AutoP purification System (Sample Manager 2767, Pump 2525, Detector: Micromass ZQ and UV 2487, solvent system: acetonitrile and 0.1% ammonium hydroxide in water; acetonitrile and 0.1% FA in water or acetonitrile and 0.1% TFA in water). Or Gilson-281 purification System (Pump 322, Detector: UV 156, solvent system: acetonitrile and 0.05% ammonium hydroxide in water; acetonitrile and 0.225% FA in water; acetonitrile and 0.05% HCl in water; acetonitrile and 0.075% TFA in water; or acetonitrile and water).

For SFC chiral separation, intermediates were separated by chiral column (Daicel chiralpak IC, 5 μm, 30×250 mm), AS (10 μm, 30×250 mm) or AD (10 μm, 30×250 mm) using Mettler Toledo Multigram III system SFC, Waters 80Q preparative SFC or Thar 80 preparative SFC, solvent system: CO$_2$ and IPA (0.5% TEA in IPA) or CO$_2$ and MeOH (0.1% NH$_3$.H$_2$O in MeOH), back pressure 100 bar, detection UV@ 254 or 220 nm.

LC/MS spectra of compounds were obtained using a LC/MS (Waters™ Alliance 2795-Micromass ZQ, Shimadzu Alliance 2020-Micromass ZQ or Agilent Alliance 6110-Micromass ZQ), LC/MS conditions were as follows (running time 3 or 1.5 mins):

Acidic condition I: A: 0.1% TFA in $H_2O$; B: 0.1% TFA in acetonitrile;
Acidic condition II: A: 0.0375% TFA in $H_2O$; B: 0.01875% TFA in acetonitrile;
Basic condition I: A: 0.1% $NH_3 \cdot H_2O$ in $H_2O$; B: acetonitrile;
Basic condition II: A: 0.025% $NH_3 \cdot H_2O$ in $H_2O$; B: acetonitrile;
Neutral condition: A: $H_2O$; B: acetonitrile.

Mass spectra (MS): generally only ions which indicate the parent mass are reported, and unless otherwise stated the mass ion quoted is the positive mass ion $(MH)^+$.

NMR Spectra were obtained using Bruker Avance 400 MHz.

The microwave assisted reactions were carried out in a Biotage Initiator Sixty microwave synthesizer. All reactions involving air-sensitive reagents were performed under an argon or nitrogen atmosphere. Reagents were used as received from commercial suppliers without further purification unless otherwise noted.

PREPARATIVE EXAMPLES

The following examples are intended to illustrate the meaning of the present invention but should by no means represent a limitation within the meaning of the present invention:

Example 1

5-[(2R,6R)-2-(5-bromo-3,4-dihydroquinazolin-2-yl)-6-methyl-morpholin-4-yl]quinoline-8-carbonitrile

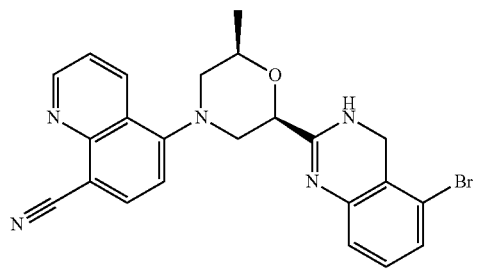 [SMILES: C[C@@H]1CN(c2ccc(C#N)c3ncccc23)C[C@H](C2=Nc3cccc(Br)c3CN2)O1]

The title compound was prepared according to the following scheme:

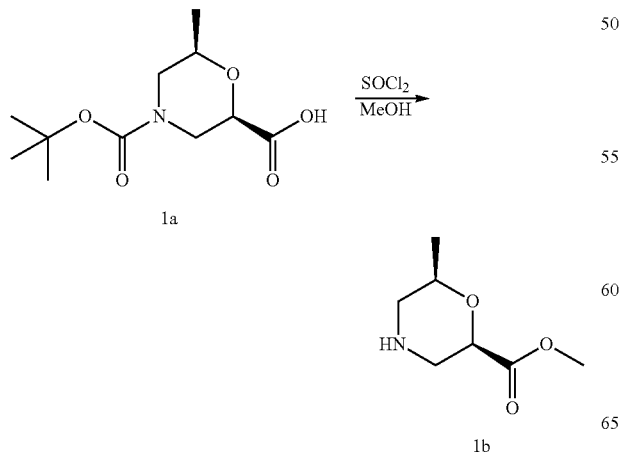

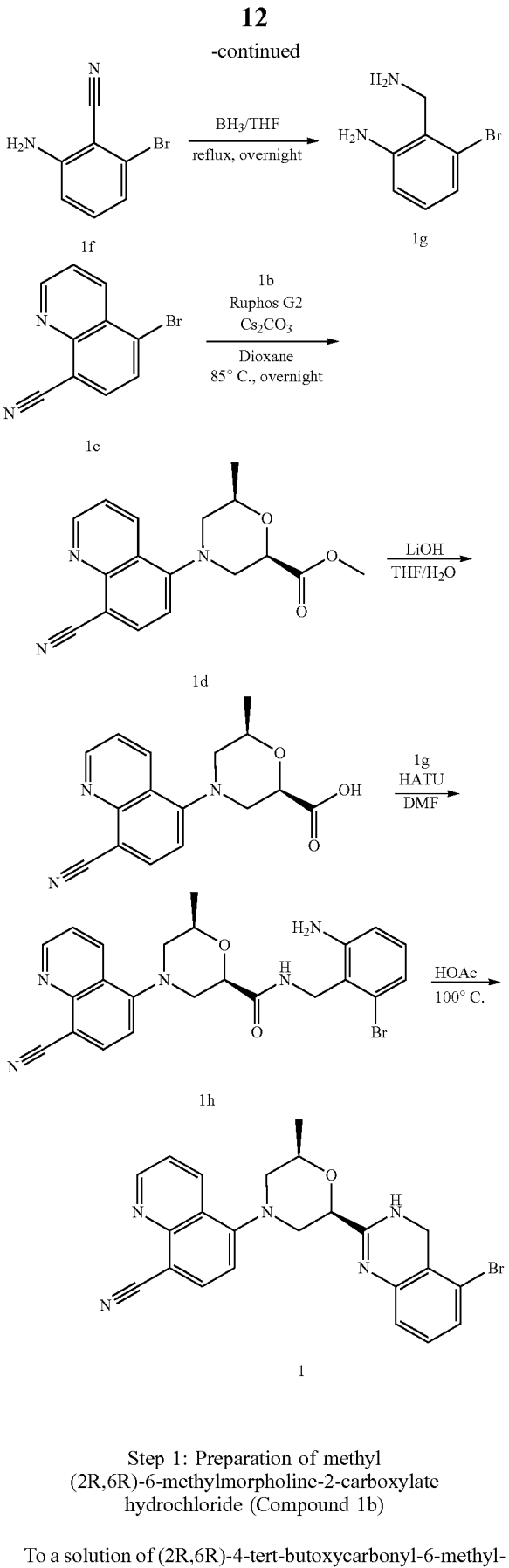

Step 1: Preparation of methyl (2R,6R)-6-methylmorpholine-2-carboxylate hydrochloride (Compound 1b)

To a solution of (2R,6R)-4-tert-butoxycarbonyl-6-methyl-morpholine-2-carboxylic acid (compound 1a, CAS:

1581752-93-3, WUXI APPTEC (Tianjin) Co., Ltd, Catalog: RC-160325, 1.5 g, 6.1 mmol) in MeOH (20 mL) was added SOCl$_2$ (1 mL) dropwise at rt. The reaction mixture was heated to reflux for 2 hrs, then cooled to rt and concentrated in vacuo to afford the crude compound 1b (1.2 g, 100% yield) as a white solid. $^1$H NMR (400 MHz, DMSO-d$_6$) δ=9.63 (br s, 2H), 4.55 (br d, J=10.88 Hz, 1H), 3.95 (br dd, J=10.21, 5.93 Hz, 1H), 3.41 (br d, J=10.64 Hz, 1H), 3.22 (br d, J=11.98 Hz, 1H), 2.94 (t, J=12.10 Hz, 1H), 2.65 (t, J=11.92 Hz, 1H), 1.16 (d, J=6.36 Hz, 3H).

Step 2: preparation of (2R,6R)-methyl 4-(8-cyano-quinolin-5-yl)-6-methylmorpholine-2-carboxylate (Compound 1d)

A mixture of 5-bromoquinoline-8-carbonitrile (compound 1c, CAS: 507476-70-2, Bepharm, Catalog: B219935, 500 mg, 2.15 mmol), (2R,6R)-methyl 6-methylmorpholine-2-carboxylate hydrochloride (compound 1b, 420 mg, 2.1 mmol), RuPhos G2 (50 mg, 0.064 mmol) and Cs$_2$CO$_3$ (1.05 g, 3.2 mmol) in dioxane (10 mL) was charged with N$_2$, and then stirred at 80° C. overnight. After the reaction mixture was cooled to rt, the solid was filtered off and the filter cake was washed with EA (10 mL) twice. The combined filtrate was concentrated in vacuo to afford the crude mixture, which was purified by silica gel column chromatography (eluted with PE:EtOAc=10:1 to 2:1) to give compound 1d (540 mg, 79% yield) as a light yellow solid. MS: calc'd 312 [(M+H)$^+$], measured 312 [(M+H)$^+$].

Step 3: preparation of (2R,6R)-4-(8-cyanoquinolin-5-yl)-6-methylmorpholine-2-carboxylic acid (Compound 1e)

To a solution of (2R,6R)-methyl 4-(8-cyanoquinolin-5-yl)-6-methylmorpholine-2-carboxylate (compound 1d, 540 mg, 1.7 mmol) in THF (10 mL) and water (10 mL) was added lithium hydroxide monohydrate (146 mg, 3.5 mmol), and the mixture was stirred at rt for 3 hrs. After THF was evaporated, the remained aqueous solution was adjusted by HCl (1 N) to pH around 6-7, and the mixture was extracted with EtOAc (20 mL) twice. The combined organic phase was dried over anhydrous Na$_2$SO$_4$, filtered and concentrated in vacuo to afford compound 1e (501 mg, 95% yield) as a light yellow solid which was directly used for next reaction without further purification. MS: calc'd 298 [(M+H)$^+$], measured 298 [(M+H)$^+$].

Step 4: Preparation of 2-(aminomethyl)-3-bromoaniline (Compound 1g)

A mixture of 2-amino-6-bromo-benzonitrile (compound 1f, 0.5 g, 2.5 mmol) and BH$_3$ (1 M in THF, 20 mL, 20 mmol) was heated to reflux for 3 hrs. After cooling, the mixture was quenched by slow addition of EtOH (5 mL) and then the solvent was removed in vacuo. The resultant residue was dissolved in EA (50 mL) and washed with aqueous solution of NaOH (0.5 N, 20 mL). The organic layer was separated and dried over anhydrous Na$_2$SO$_4$, filtered and concentrated in vacuo to afford compound 1g (480 mg, 95% yield) as a light brown waxy solid, which was directly used for next step without further purification. MS: calc'd 201 and 203 [(M+H)$^+$], measured 201 and 203 [(M+H)$^+$].

Step 5: preparation of (2R,6R)—N-(2-amino-6-bromobenzyl)-4-(8-cyanoquinolin-5-yl)-6-methyl-morpholine-2-carboxamide (Compound 1h)

To a mixture of (2R,6R)-4-(8-cyanoquinolin-5-yl)-6-methylmorpholine-2-carboxylic acid (compound 1e, 100 mg, 0.34 mmol), 2-(aminomethyl)-3-bromoaniline (compound 1g, 67.6 mg, 0.34 mmol), HATU (153 mg, 0.40 mmol) in DMF (5 mL) was added DIPEA (65.2 mg, 0.50 mmol), and the reaction mixture was stirred for 2 hrs at rt. After the solvent was removed in vacuo, the residue was dissolved in EtOAc (30 mL) and washed with water (10 mL). The organic layer was separated and dried over anhydrous Na$_2$SO$_4$, filtered and concentrated in vacuo. The residue was purified by silica gel column chromatography (eluted with PE:EtOAc=10:1 to 2:1) to give compound 1h (130 mg, 80% yield) as a light yellow solid. MS: calc'd 480 and 482 [(M+H)$^+$], measured 480 and 482 [(M+H)$^+$].

Step 6: Preparation of 5-[(2R,6R)-2-(5-bromo-3,4-dihydroquinazolin-2-yl)-6-methyl-morpholin-4-yl]quinoline-8-carbonitrile (Example 1)

A solution of (2R,6R)—N-(2-amino-6-bromobenzyl)-4-(8-cyanoquinolin-5-yl)-6-methylmorpholine-2-carboxamide (compound 1h, 130 mg, 0.27 mmol) in AcOH (5 mL) was stirred at 100° C. for 3 hrs. After cooled to rt, the solvent was evaporated in vacuo and the residue was dissolved in EtOAc (30 mL), then washed with aqueous solution of NaHCO$_3$ (1N, 10 mL).

The organic layer was separated and dried over anhydrous Na$_2$SO$_4$, filtered and concentrated in vacuo. The residue was purified by silica gel column chromatography (eluted with PE:EtOAc=10:3 to 0:1) to afford Example 1 (110 mg, 86% yield) as a light yellow solid. MS: calc'd 462 and 464 [(M+H)$^+$], measured 462 and 464 [(M+H)$^+$]. $^1$H NMR (400 MHz, METHANOL-d$_4$) δ=9.02 (dd, J=4.22, 1.53 Hz, 1H), 8.74 (dd, J=8.56, 1.59 Hz, 1H), 8.17 (d, J=7.95 Hz, 1H), 7.70 (dd, J=8.56, 4.28 Hz, 1H), 7.32 (d, J=8.07 Hz, 1H), 7.22 (d, J=8.07 Hz, 1H), 7.04 (t, J=7.95 Hz, 1H), 6.86 (d, J=7.95 Hz, 1H), 4.58-4.73 (m, 3H), 4.20 (ddd, J=10.12, 6.27, 2.20 Hz, 1H), 3.70 (br d, J=12.10 Hz, 1H), 3.44 (br d, J=12.10 Hz, 1H), 2.96 (t, J=11.31 Hz, 1H), 2.81 (dd, J=11.92, 10.33 Hz, 1H), 1.38 (d, J=6.24 Hz, 3H).

Example 2

5-[(2R,6R)-2-(6-bromo-3,4-dihydroquinazolin-2-yl)-6-methyl-morpholin-4-yl]quinoline-8-carbonitrile

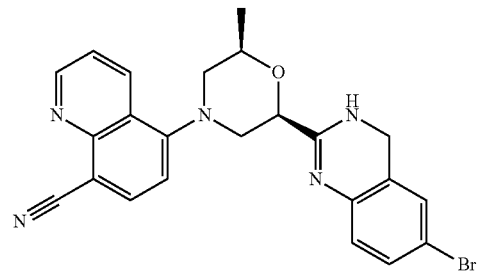 [SMILES: C[C@@H]1CN(c2ccc(C#N)c3ncccc23)C[C@H](C2=Nc3ccc(Br)cc3CN2)O1]

The title compound was prepared in analogy to the preparation of Example 1 by using 2-amino-5-bromo-benzonitrile instead of 2-amino-6-bromo-benzonitrile (compound 1f). Example 2 (301 mg) was obtained as a light yellow solid. MS: calc'd 462 and 464 [(M+H)$^+$], measured 462 and 464 [(M+H)$^+$]. $^1$H NMR (400 MHz, METHANOL-d$_4$) δ=9.01 (dd, J=4.22, 1.65 Hz, 1H), 8.73 (dd, J=8.62, 1.65 Hz, 1H), 8.16 (d, J=8.07 Hz, 1H), 7.69 (dd, J=8.56, 4.28 Hz, 1H), 7.30 (d, J=8.07 Hz, 1H), 7.26 (dd, J=8.44, 2.32 Hz, 1H), 7.09-7.14 (m, 1H), 6.82 (d, J=8.44 Hz, 1H), 4.59-4.66 (m, 3H), 4.19 (ddd, J=10.15, 6.30, 2.26 Hz, 1H), 3.69 (dt, J=11.98, 2.14 Hz, 1H), 3.39-3.47 (m, 1H), 2.94 (dd, J=11.92, 10.70 Hz, 1H), 2.80 (dd, J=11.98, 10.27 Hz, 1H), 1.37 (d, J=6.24 Hz, 3H).

Example 3

5-[(2R,6R)-2-(1,4-dihydroquinazolin-2-yl)-6-methyl-morpholin-4-yl]quinoline-8-carbonitrile

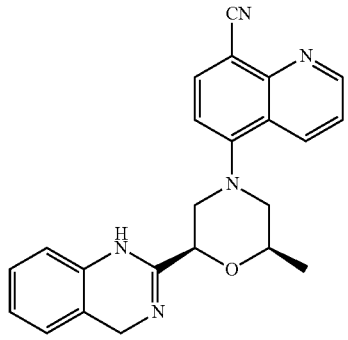 [SMILES: C[C@@H]1CN(c2ccc(C#N)c3ncccc23)C[C@H](C2=NCc3ccccc3N2)O1]

The title compound was prepared in analogy to the preparation of Example 1 by using 2-aminobenzonitrile instead of 2-amino-6-bromo-benzonitrile (compound 1f).

Example 3

(13.5 mg) was obtained as a yellow solid. MS: calc'd 384 [(M+H)$^+$], measured 384 [(M+H)$^+$] $^1$H NMR (400 MHz, METHANOL-$d_4$) δ 9.01-9.07 (m, 1H), 8.75 (dd, J=1.57, 8.60 Hz, 1H), 8.20 (dd, J=2.20, 7.97 Hz, 1H), 7.72 (ddd, J=1.07, 4.27, 8.60 Hz, 1H), 7.26-7.41 (m, 3H), 7.19-7.24 (m, 1H), 7.13 (d, J=7.91 Hz, 1H), 5.03 (br d, J=10.54 Hz, 1H), 4.90-4.94 (m, 2H), 4.27-4.37 (m, 1H), 3.75 (br d, J=11.80 Hz, 1H), 3.51 (br d, J=12.05 Hz, 1H), 3.15 (t, J=11.23 Hz, 1H), 2.86 (dd, J=10.42, 12.30 Hz, 1H), 1.42 (d, J=6.27 Hz, 3H).

Example 4

5-[(2R,6R)-2-(7-bromo-3,4-dihydroquinazolin-2-yl)-6-methyl-morpholin-4-yl]quinoline-8-carbonitrile

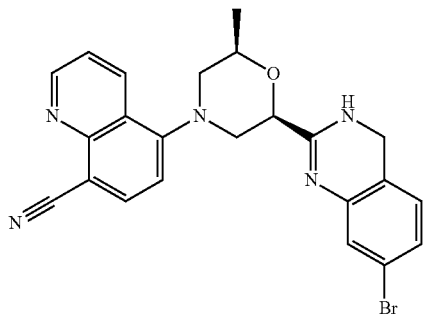 [SMILES: C[C@@H]1CN(c2ccc(C#N)c3ncccc23)C[C@H](C2=Nc3cc(Br)ccc3CN2)O1]

The title compound was prepared in analogy to the preparation of Example 1 by using 2-amino-4-bromo-benzonitrile instead of 2-amino-6-bromo-benzonitrile (compound 1f). Example 4 (130 mg) was obtained as a light yellow solid. MS: calc'd 462 and 464 [(M+H)$^+$], measured 462 and 464 [(M+H)$^+$]. $^1$H NMR (400 MHz, METHANOL-$d_4$) δ=9.02 (dd, J=4.22, 1.65 Hz, 1H), 8.74 (dd, J=8.56, 1.71 Hz, 1H), 8.17 (d, J=8.07 Hz, 1H), 7.70 (dd, J=8.56, 4.28 Hz, 1H), 7.31 (d, J=8.07 Hz, 1H), 7.12 (dd, J=8.07, 1.96 Hz, 1H), 7.05 (d, J=1.96 Hz, 1H), 6.86 (d, J=8.07 Hz, 1H), 4.54-4.64 (m, 3H), 4.20 (ddd, J=10.18, 6.27, 2.26 Hz, 1H), 3.70 (br d, J=11.98 Hz, 1H), 3.40-3.47 (m, 1H), 2.94 (dd, J=11.86, 10.76 Hz, 1H), 2.77-2.85 (m, 1H), 1.38 (d, J=6.24 Hz, 3H).

Example 5

5-[(2R,6R)-2-(8-bromo-3,4-dihydroquinazolin-2-yl)-6-methyl-morpholin-4-yl]quinoline-8-carbonitrile

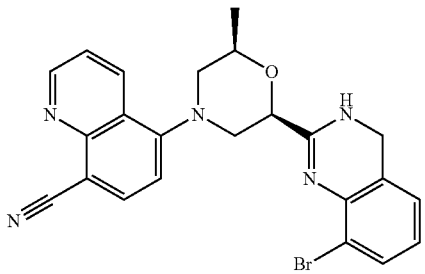 [SMILES: C[C@@H]1CN(c2ccc(C#N)c3ncccc23)C[C@H](C2=Nc3c(Br)cccc3CN2)O1]

The title compound was prepared in analogy to the preparation of Example 1 by using 2-amino-3-bromo-benzonitrile instead of 2-amino-6-bromo-benzonitrile (compound 1f). Example 5 (130 mg) was obtained as a light yellow solid. MS: calc'd 462 and 464 [(M+H)$^+$], measured 462 and 464 [(M+H)$^+$]. $^1$H NMR (400 MHz, METHANOL-$d_4$) δ=9.02 (dd, J=4.16, 1.59 Hz, 1H), 8.77 (br d, J=8.44 Hz, 1H), 8.17 (d, J=7.95 Hz, 1H), 7.70 (dd, J=8.56, 4.28 Hz, 1H), 7.39 (br d, J=8.07 Hz, 1H), 7.31 (d, J=8.07 Hz, 1H), 6.85-7.01 (m, 2H), 4.74 (dd, J=10.45, 2.63 Hz, 1H), 4.62 (s, 2H) 4.24 (br s, 1H), 3.78 (br d, J=12.47 Hz, 1H), 3.46 (br d, J=11.98 Hz, 1H), 2.93 (t, J=11.31 Hz, 1H), 2.81 (br t, J=11.25 Hz, 1H), 1.39 (d, J=6.24 Hz, 3H).

Example 6

5-[(2R,6R)-2-methyl-6-(5-piperazin-1-yl-3,4-dihydroquinazolin-2-yl)morpholin-4-yl]quinoline-8-carbonitrile

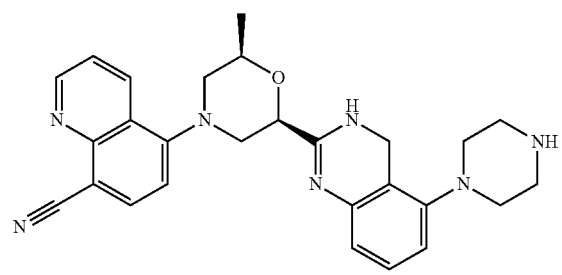 [SMILES: C[C@@H]1CN(c2ccc(C#N)c3ncccc23)C[C@H](C2=Nc3cccc(N4CCNCC4)c3CN2)O1]

The title compound was prepared according to the following scheme:
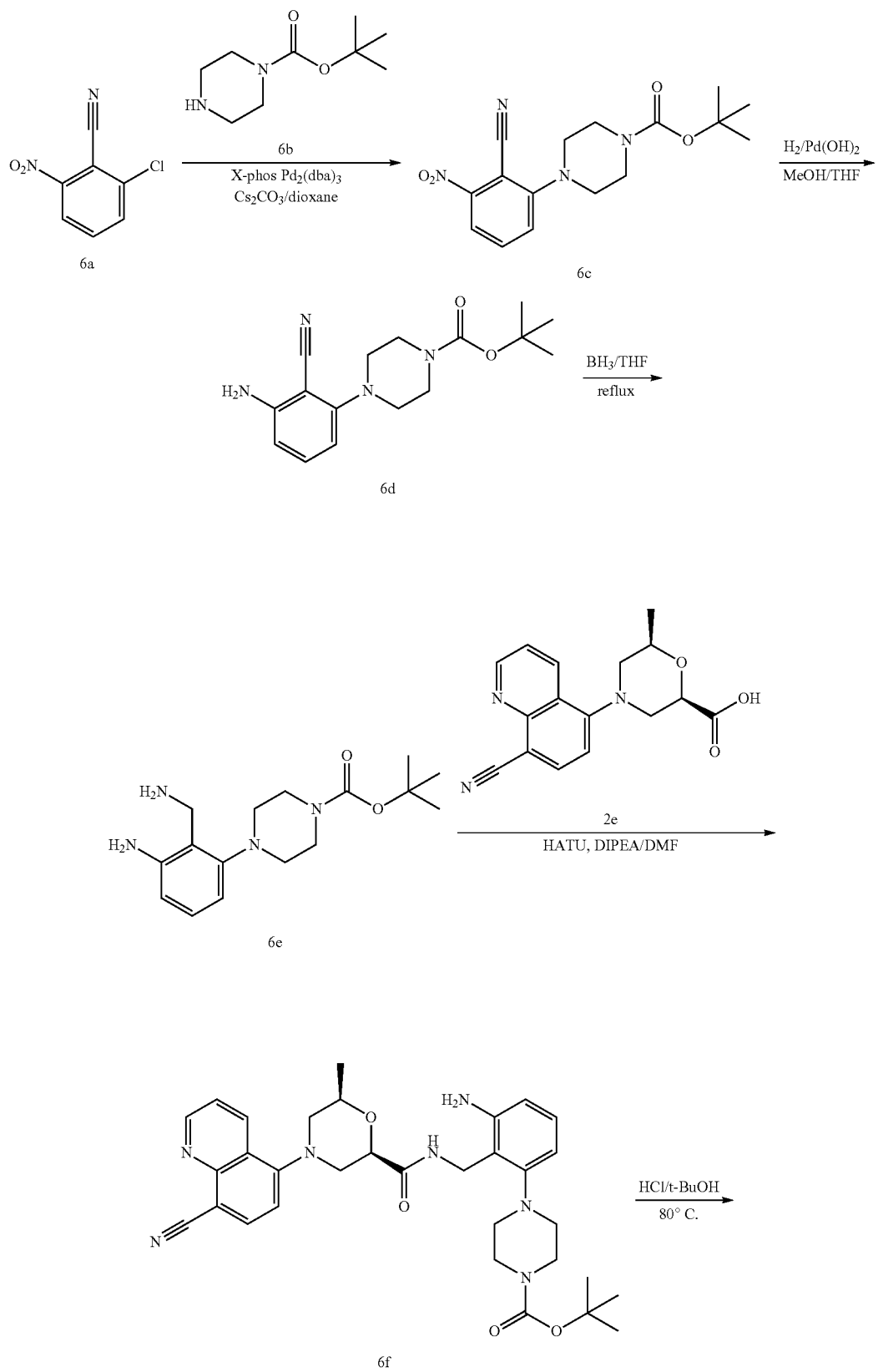

-continued

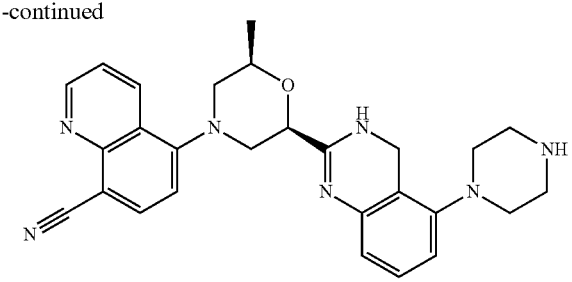

6

Step 1: Preparation of methyl tert-butyl 4-(2-cyano-3-nitrophenyl)piperazine-1-carboxylate (Compound 6c)

A mixture of 2-chloro-6-nitrobenzonitrile (compound 6a, 1.1 g, 6.0 mmol), tert-butyl piperazine-1-carboxylate (compound 6b, 1.2 g, 6.6 mmol), $Cs_2CO_3$ (2.9 g, 9.0 mmol), $Pd_2(dba)_3$ (110 mg, 0.12 mmol) and Xantphos (105 mg, 0.18 mmol) in dioxane (20 mL) was charged with $N_2$ and stirred at 80° C. overnight. After cooled to rt, the reaction mixture was filtered and the filter cake was washed with EtOAc (20 mL). The combined filtrate was concentrated in vacuo to afford the crude residue, which was purified by silica gel column chromatography (eluted with PE:EtOAc=10:1 to 1:1) to afford compound 6c (1.5 g, 75% yield) as a light yellow solid. MS: calc'd 333 [(M+H)$^+$], measured 333 [(M+H)$^+$].

Step 2: Preparation of tert-butyl 4-(3-amino-2-cyanophenyl)piperazine-1-carboxylate (Compound 6d)

A mixture of tert-butyl 4-(2-cyano-3-nitrophenyl)piperazine-1-carboxylate (compound 6c, 1.5 g, 4.5 mmol) and $Pd(OH)_2$ (31.7 mg, 0.23 mmol) in MeOH (15 mL) and THF (15 mL) was stirred in a hydrogen atmosphere overnight. After the catalyst was filtered off, the filtrate was concentrated in vacuo to afford compound 6d (1.3 g, 95% yield) as a light brown waxy solid, which was directly used for next reaction without further purification. MS: calc'd 303 [(M+H)$^+$], measured 303 [(M+H)$^+$].

Step 3: Preparation of tert-butyl 4-(3-amino-2-(aminomethyl)phenyl)piperazine-1-carboxylate (Compound 6e)

A mixture of tert-butyl 4-(3-amino-2-cyanophenyl)piperazine-1-carboxylate (compound 6e, 0.5 g, 1.6 mmol) and $BH_3$ (1 M in THF, 20 mL, 20 mmol) was heated to reflux for 3 hrs. After cooled to rt, the reaction was quenched by addition of EtOH (5 mL) dropwise and the solvent was removed in vacuo. The resultant residue was dissolved in EtOAc (50 mL) and washed with aqueous NaOH (0.5 N, 20 mL), dried over anhydrous $Na_2SO_4$, filtered and concentrated in vacuo to afford compound 6e (450 mg, 88% yield) as a light brown waxy solid, which was directly used for the next step without further purification. MS: calc'd 307 [(M+H)$^+$], measured 307 [(M+H)$^+$].

Step 4: Preparation of tert-butyl 4-(3-amino-2-(((2R,6R)-4-(8-cyanoquinolin-5-yl)-6-methylmorpholine-2-carboxamido)methyl)phenyl)piperazine-1-carboxylate (Compound 6f)

To a mixture of (2R,6R)-4-(8-cyanoquinolin-5-yl)-6-methylmorpholine-2-carboxylic acid (compound 2e, 150 mg, 0.51 mmol), tert-butyl 4-(3-amino-2-(aminomethyl)phenyl)piperazine-1-carboxylate (compound 6e, 155 mg, 0.51 mmol), HATU (230 mg, 0.61 mmol) in DMF (5 mL) was added DIPEA (130 mg, 1.00 mmol), and the reaction mixture was stirred at rt for 2 hrs. After the solvent was removed in vacuo, the residue was dissolved in EtOAc (30 mL) and washed with water (10 mL), dried over anhydrous $Na_2SO_4$, filtered and concentrated in vacuo. The residue was purified by silica gel column chromatography (eluted with PE:EtOAc=10:3 to 0:1) to afford compound 6f (201 mg, 68% yield) as a light yellow solid. MS: calc'd 586 [(M+H)$^+$], measured 586 [(M+H)$^+$].

Step 5: Preparation of 5-[(2R,6R)-2-methyl-6-(5-piperazin-1-yl-3,4-dihydroquinazolin-2-yl)morpholin-4-yl]quinoline-8-carbonitrile (Example 6)

To a solution of tert-butyl 4-(3-amino-2-(((2R,6R)-4-(8-cyanoquinolin-5-yl)-6-methylmorpholine-2-carboxamido)methyl)phenyl)piperazine-1-carboxylate (compound 6f, 140 mg, 0.24 mmol) in tert-butanol (10 mL) was added concentrated HCl (1 mL), and the mixture was stirred at 80° C. for 2 hrs. After cool to rt, the solvent was removed in vacuo to afford the crude product which was washed with EtOAc (5 mL). The solid was collected by filtration and air-dried to afford Example 6 (120 mg, 88% yield) as a light brown solid. MS: calc'd 468 [(M+H)$^+$], measured 468 [(M+H)$^+$]. $^1$H NMR (400 MHz, METHANOL-d$_4$) δ=9.10 (dd, J=4.46, 1.53 Hz, 1H), 8.97 (dd, J=8.62, 1.53 Hz, 1H), 8.28 (d, J=8.07 Hz, 1H), 7.85 (dd, J=8.68, 4.52 Hz, 1H), 7.46 (d, J=8.07 Hz, 1H), 7.35-7.43 (m, 1H), 7.19 (d, J=7.70 Hz, 1H), 7.01 (d, J=7.70 Hz, 1H), 5.10 (dd, J=10.51, 2.57 Hz, 1H), 4.85-4.89 (m, 1H), 4.28-4.38 (m, 1H), 3.83 (br d, J=11.86 Hz, 1H), 3.48-3.65 (m, 2H), 3.38-3.45 (m, 4H), 3.11-3.22 (m, 5H), 2.92 (dd, J=12.29, 10.45 Hz, 1H), 1.43 (d, J=6.24 Hz, 3H).

Example 7

5-[(2R,6R)-2-methyl-6-(6-piperazin-1-yl-3,4-dihydroquinazolin-2-yl)morpholin-4-yl]quinoline-8-carbonitrile

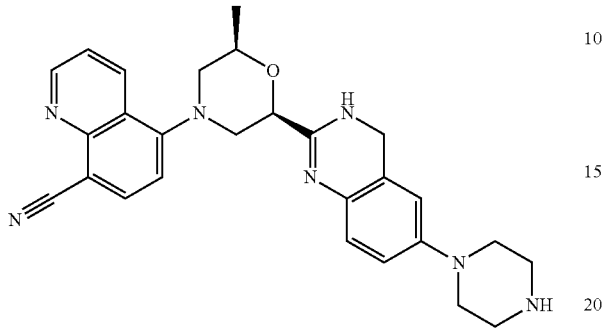

The title compound was prepared in analogy to the preparation of Example 6 by using 5-chloro-2-nitrobenzonitrile instead of 2-chloro-6-nitrobenzonitrile (compound 6a). Example 7 (12 mg) was obtained as a light brown solid. MS: calc'd 468 [(M+H)$^+$], measured 468 [(M+H)$^+$]. $^1$H NMR (400 MHz, METHANOL-d$_4$) δ=9.38 (br d, J=8.19 Hz, 1H), 9.23 (br d, J=4.28 Hz, 1H), 8.45 (br d, J=7.83 Hz, 1H), 8.11 (br d, J=5.01 Hz, 1H), 7.61 (br d, J=8.07 Hz, 1H), 7.19 (br d, J=8.68 Hz, 1H), 7.02 (br d, J=8.31 Hz, 1H), 6.92 (br s, 1H), 5.17 (br d, J=9.29 Hz, 1H), 4.87 (s, 2H), 4.32 (br d, J=11.49 Hz, 1H), 3.95 (br d, J=10.88 Hz, 1H), 3.59-3.54 (m, 2H), 3.51-3.47 (m, 4H), 3.43-3.38 (m, 4H), 3.24 (br t, J=9.60 Hz, 1H), 1.43 (d, J=5.87 Hz, 3H).

Example 8

5-[(2R,6R)-2-methyl-6-(7-piperazin-1-yl-3,4-dihydroquinazolin-2-yl)morpholin-4-yl]quinoline-8-carbonitrile

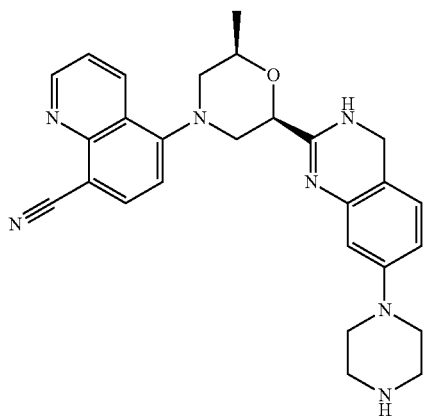 [SMILES: C[C@@H]1CN(c2ccc(C#N)c3ncccc23)C[C@H](C2=Nc3cc(N4CCNCC4)ccc3CN2)O1]

The title compound was prepared in analogy to the preparation of Example 6 by using 4-chloro-2-nitrobenzonitrile instead of 2-chloro-6-nitrobenzonitrile (compound 6a). Example 8 (24 mg) was obtained as a light brown solid. MS: calc'd 468 [(M+H)$^+$], measured 468 [(M+H)$^+$]. $^1$H NMR (400 MHz, METHANOL-d$_4$) δ=9.56 (br d, J=8.31 Hz, 1H), 9.29 (br d, J=4.77 Hz, 1H), 8.51 (d, J=8.19 Hz, 1H), 8.23 (br dd, J=8.19, 5.26 Hz, 1H), 7.68 (br d, J=8.07 Hz, 1H), 7.12 (d, J=8.44 Hz, 1H), 6.91-7.01 (m, 2H), 5.24 (br d, J=9.90 Hz, 1H), 4.82 (s, 2H), 4.35 (br d, J=6.48 Hz, 1H), 4.05 (br d, J=11.62 Hz, 1H), 3.59-3.66 (m, 1H), 3.51 (br dd, J=5.99, 3.42 Hz, 4H), 3.37-3.46 (m, 4H), 3.22-3.31 (m, 1H), 3.07-3.16 (m, 1H), 1.45 (d, J=5.99 Hz, 3H).

Example 9

5-[(2R,6R)-2-methyl-6-(8-piperazin-1-yl-3,4-dihydroquinazolin-2-yl)morpholin-4-yl]quinoline-8-carbonitrile

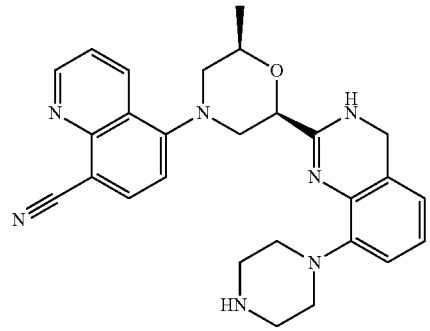 [SMILES: C[C@@H]1CN(c2ccc(C#N)c3ncccc23)C[C@H](C2=Nc3c(cccc3N3CCNCC3)CN2)O1]

The title compound was prepared in analogy to the preparation of Example 6 by using 3-chloro-2-nitrobenzonitrile instead of 2-chloro-6-nitrobenzonitrile (compound 6a). Example 9 (10 mg) was obtained as a light brown solid. MS: calc'd 468 [(M+H)$^+$], measured 468 [(M+H)$^+$]. $^1$H NMR (400 MHz, METHANOL-d$_4$) δ=9.02 (dd, J=4.28, 1.59 Hz, 1H) 8.79 (dd, J=8.56, 1.71 Hz, 1H) 8.16 (d, J=8.07 Hz, 1H) 7.72 (dd, J=8.56, 4.16 Hz, 1H) 7.29-7.38 (m, 3H) 7.08 (t, J=4.40 Hz, 1H) 5.33 (dd, J=10.39, 2.57 Hz, 1H) 4.91 (s, 2H) 4.36 (ddd, J=10.27, 6.36, 2.20 Hz, 1H) 3.77 (br d, J=11.74 Hz, 1H) 3.38-3.57 (m, 5H) 3.07-3.24 (m, 5H) 2.82 (dd, J=12.35, 10.39 Hz, 1H) 1.43 (d, J=6.36 Hz, 3H).

Example 10

5-[(2R,6R)-2-[5-(4-hydroxy-1-piperidyl)-3,4-dihydroquinazolin-2-yl]-6-methyl-morpholin-4-yl]quinoline-8-carbonitrile

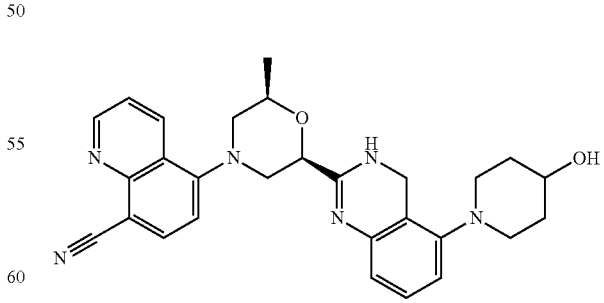

The title compound was prepared in analogy to the preparation of Example 6 by using piperidin-4-ol instead of tert-butyl piperazine-1-carboxylate (compound 6b). Example 10 (5 mg) was obtained as a light brown solid. MS: calc'd 483 [(M+H)$^+$], measured 483 [(M+H)$^+$]. $^1$H NMR (400 MHz, METHANOL-d₄) δ=9.04 (dd, J=4.22, 1.53 Hz, 1H), 8.75 (dd, J=8.56, 1.59 Hz, 1H), 8.20 (d, J=7.95 Hz, 1H), 7.72 (dd, J=8.62, 4.22 Hz, 1H), 7.38 (d, J=8.07 Hz, 1H), 7.32 (t, J=8.07 Hz, 1H), 7.10-7.13 (m, 1H), 6.85 (d, J=7.34 Hz, 1H), 5.02 (dd, J=10.58, 2.63 Hz, 1H), 4.83 (d, J=3.42 Hz, 2H), 4.33 (ddd, J=10.15, 6.30, 2.26 Hz, 1H) 3.70-3.82 (m, 2H), 3.51 (br d, J=12.35 Hz, 1H), 3.15 (t, J=11.25 Hz, 1H), 2.99-3.07 (m, 2H), 2.92 (s, 1H), 2.82-2.90 (m, 1H), 2.70-2.81 (m, 2H), 1.95-2.03 (m, 2H), 1.63-1.75 (m, 2H), 1.42 (d, J=6.24 Hz, 3H).

Example 11

5-[(2R,6R)-2-methyl-6-(5-morpholino-3,4-dihydro-quinazolin-2-yl)morpholin-4-yl]quinoline-8-carbonitrile

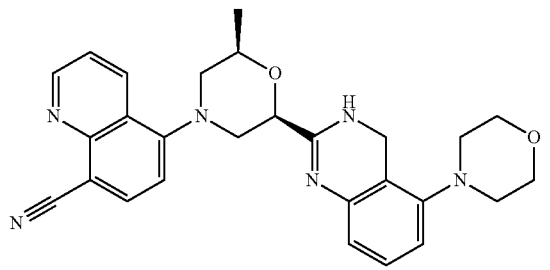 [SMILES: C[C@@H]1CN(c2ccc(C#N)c3ncccc23)C[C@H](C2=Nc3cccc(N4CCOCC4)c3CN2)O1]

The title compound was prepared in analogy to the preparation of Example 6 by using morpholine instead of tert-butyl piperazine-1-carboxylate (compound 6b). Example 11 (21 mg) was obtained as a light brown solid. MS: calc'd 469 [(M+H)⁺], measured 469 [(M+H)⁺]. ¹H NMR (400 MHz, METHANOL-d₄) δ=9.42 (br d, J=7.70 Hz, 1H), 9.23 (br d, J=3.67 Hz, 1H), 8.46 (br d, J=7.09 Hz, 1H), 8.15 (br s, 1H), 7.63 (br d, J=7.46 Hz, 1H), 7.37 (t, J=7.95 Hz, 1H), 7.18 (d, J=8.07 Hz, 1H), 7.04 (d, J=7.82 Hz, 1H), 5.21 (br d, J=8.07 Hz, 1H), 4.82-4.97 (m, 2H), 4.34 (br s, 1H), 3.97 (br d, J=7.70 Hz, 1H), 3.87 (br s, 4H), 3.60 (br d, J=11.98 Hz, 1H), 3.26 (br s, 1H), 3.05 (br t, J=10.70 Hz, 1H), 2.91-3.00 (m, 4H), 1.44 (br d, J=5.62 Hz, 3H).

Example 12

5-[(2R,6R)-2-methyl-6-[5-(4-methylpiperazin-1-yl)-3,4-dihydroquinazolin-2-yl]morpholin-4-yl]quinoline-8-carbonitrile

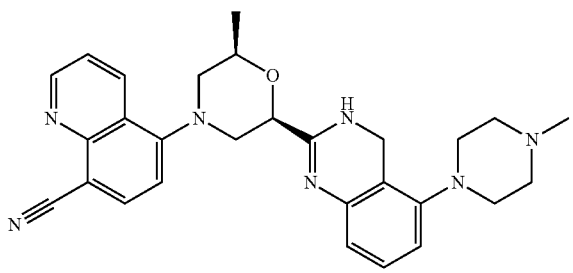 [SMILES: C[C@@H]1CN(c2ccc(C#N)c3ncccc23)C[C@H](C2=Nc3cccc(N4CCN(C)CC4)c3CN2)O1]

The title compound was prepared in analogy to the preparation of Example 6 by using 1-methylpiperazine instead of tert-butyl piperazine-1-carboxylate (compound 6b). Example 12 (11 mg) was obtained as a light brown solid. MS: calc'd 482 [(M+H)⁺], measured 482 [(M+H)⁺]. ¹H NMR (400 MHz, METHANOL-d₄) δ=9.01 (d, J=3.18 Hz, 1H), 8.74 (br d, J=7.82 Hz, 1H), 8.17 (d, J=7.95 Hz, 1H), 7.71 (dd, J=8.44, 4.16 Hz, 1H), 7.28-7.40 (m, 2H), 7.14 (d, J=7.95 Hz, 1H), 6.95 (d, J=7.95 Hz, 1H), 5.05 (br d, J=9.41 Hz, 1H), 4.85 (br d, J=4.89 Hz, 2H), 4.25-4.36 (m, 1H), 3.78 (br d, J=11.62 Hz, 1H), 3.49 (br d, J=12.10 Hz, 1H), 3.27 (br s, 4H), 3.06-3.16 (m, 5H), 2.86-2.91 (m, 1H), 2.84 (s, 3H), 1.42 (d, J=6.11 Hz, 3H).

Example 13

5-[(2R,6R)-2-[5-(2,7-diazaspiro[4.4]nonan-2-yl)-3,4-dihydroquinazolin-2-yl]-6-methyl-morpholin-4-yl]quinoline-8-carbonitrile

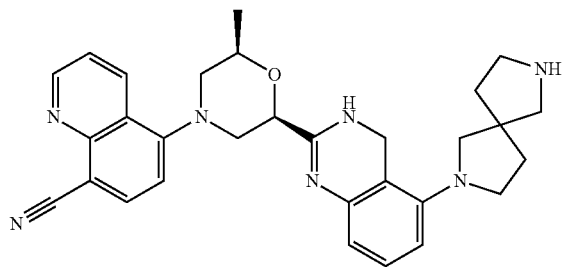 [SMILES: C[C@@H]1CN(c2ccc(C#N)c3ncccc23)C[C@H](C2=Nc3cccc(N4CCC5(CCNC5)C4)c3CN2)O1]

The title compound was prepared in analogy to the preparation of Example 6 by using tert-butyl 2,7-diazaspiro[4.4]nonane-2-carboxylate instead of tert-butyl piperazine-1-carboxylate (compound 6b). Example 13 (16 mg) was obtained as a light brown solid. MS: calc'd 508 [(M+H)⁺], measured 508 [(M+H)⁺]. ¹H NMR (400 MHz, METHANOL-d₄) δ=9.38 (br d, J=8.19 Hz, 1H), 9.22 (br d, J=4.65 Hz, 1H), 8.44 (br d, J=8.07 Hz, 1H), 8.12 (br dd, J=8.19, 4.89 Hz, 1H), 7.61 (br d, J=8.07 Hz, 1H), 7.28 (t, J=8.07 Hz, 1H), 7.05 (d, J=8.31 Hz, 1H), 6.89 (d, J=7.82 Hz, 1H), 5.20 (br d, J=9.41 Hz, 1H), 4.92 (br s, 1H), 4.34 (br s, 1H), 3.96 (br d, J=11.25 Hz, 1H), 3.59 (br d, J=12.10 Hz, 1H), 3.36-3.53 (m, 7H), 3.22-3.30 (m, 1H), 3.04 (br t, J=11.31 Hz, 1H), 2.09-2.28 (m, 4H), 1.44 (d, J=5.99 Hz, 3H), 1.27-1.34 (m, 2H).

Example 14

5-[(2R,6R)-2-(6-bromo-4,5-dihydro-3H-1,3-benzo-diazepin-2-yl)-6-methyl-morpholin-4-yl]quinoline-8-carbonitrile

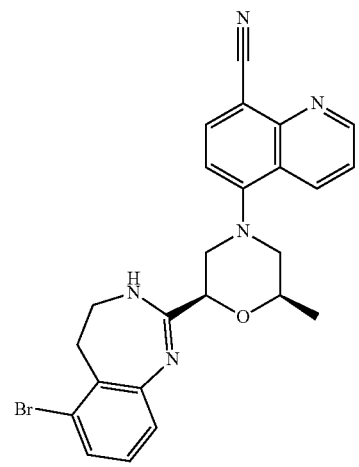 [SMILES: C[C@@H]1CN(c2ccc(C#N)c3ncccc23)C[C@H](C2=Nc3cccc(Br)c3CCN2)O1]

The title compound was prepared according to the scheme below:

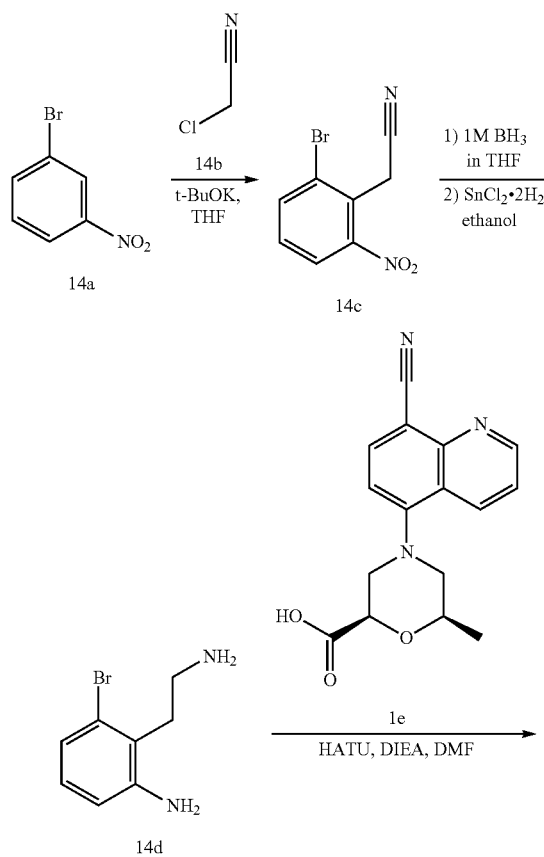

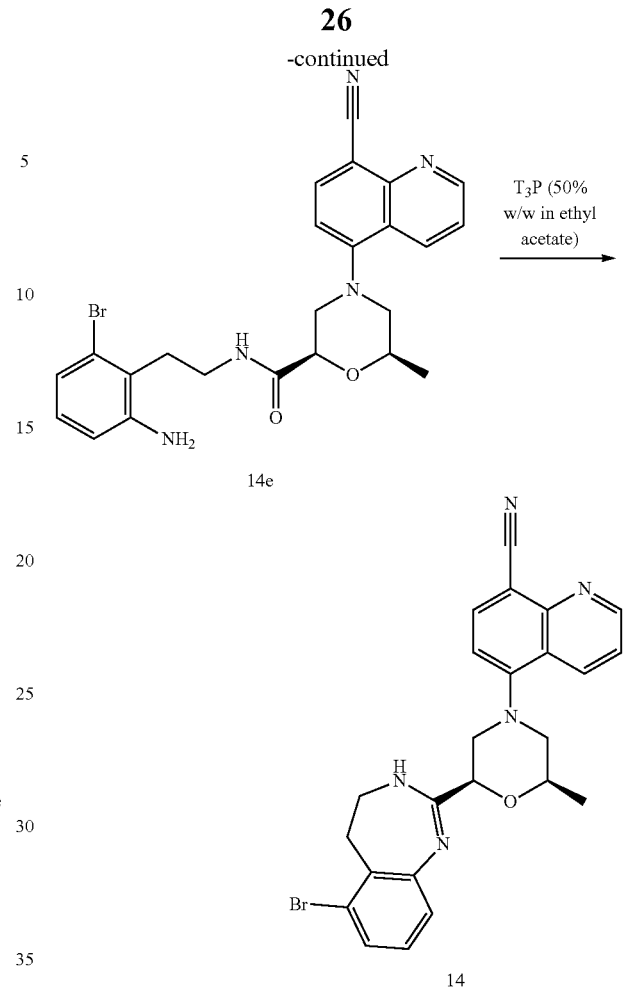

Step 1: Preparation of 2-(2-bromo-6-nitro-phenyl)acetonitrile (Compound 14c)

To a cooled solution of potassium tert-butoxide (1.2 g, 10.1 mmol) in THF (10 mL), a solution of 2-chloroacetonitrile (compound 14b, 375 mg, 5.0 mmol) and 1-bromo-3-nitrobenzene (compound 14a, 1.0 g, 5.0 mmol) in THF (10 mL) was added within 10 mins. During the addition the reaction temperature was kept at −10° C. to −20° C. About 10 mins after the addition was completed, the mixture was acidified with aq. HCl (1 N) to pH around 5. The resultant mixture was extracted with DCM (100 mL) twice, and the organic layer was washed with water and brine, dried over $Na_2SO_4$, filtered and concentrated in vacuo. The crude product was purified by silica gel column chromatography (eluted with PE:EtOAc=10:1 to 5:1) to give compound 14c (710 mg, 59% yield) as a yellow solid. MS: calc'd 239 and 241 [(M−H)⁻], measured 239 and 241 [(M−H)⁻].

Step 2: Preparation of 2-(2-aminoethyl)-3-bromo-aniline (Compound 14d)

A mixture of 2-(2-bromo-6-nitro-phenyl)acetonitrile (compound 14c, 710 mg, 2.9 mmol) and $BH_3$ solution (1 M in THF, 25 mL, 25 mmol) was stirred at 75° C. for 4 hrs, then HCl solution (6 N, 25 mL) was added to the reaction mixture at 0° C. After the organic solvent was removed in vacuo, the aqueous phase was basified with NaOH solution (4 N) to pH 10, then extracted with EtOAc (20 mL) twice. The organic layer was washed with brine (10 mL), dried over MgSO$_4$, filtered and concentrated in vacuo to afford a brown residue. Without further purification, the residue was mixed with SnCl$_2$.2H$_2$O (3.27 g, 14.5 mmol) and absolute ethanol (20 mL) and heated at 70° C. for 2 hrs. After cooled to rt, the reaction mixture was poured into ice (100 g) and the pH was adjusted to around 8 by addition of a NaHCO$_3$ solution (5%). The resultant basic mixture was stirred for 1 hr and then extracted by EA (50 mL) three times. The combined organic layer was washed with water (50 mL), dried over MgSO$_4$, filtered and concentrated in vacuo to afford compound 14d (310 mg, 50% yield) as a brown oil. MS: calc'd 215 and 217 [(M+H)$^+$], measured 215 and 217 [(M+H)$^+$].

Step 3: Preparation of (2R,6R)—N-[2-(2-amino-6-bromo-phenyl)ethyl]-4-(8-cyano-5-quinolyl)-6-methyl-morpholine-2-carboxamide (Compound 14e)

To a solution of 2-(2-aminoethyl)-3-bromo-aniline (compound 14d, 120 mg, 0.56 mmol), (2R,6R)-4-(8-cyano-5-quinolyl)-6-methyl-morpholine-2-carboxylic acid (compound 1e, 83 mg, 0.28 mmol) and DIPEA (0.15 mL, 0.84 mmol) in DMF (5 mL) was added HATU (106 mg, 0.28 mmol) and the mixture was stirred at rt for 30 mins. The mixture was diluted with water (30 mL) and extracted EtOAc (20 mL) three times, and the combined organic layer was washed with brine, dried over Na$_2$SO$_4$, filtered and concentrated in vacuo. The residue was purified by silica gel column chromatography (eluted with PE:EtOAc=3:1 to 1:2) to afford compound 14e (110 mg, 79% yield) as a yellow solid. MS: calc'd 494 and 496 [(M+H)$^+$], measured 494 and 496 [(M+H)$^+$].

Step 4: Preparation of 5-[(2R,6R)-2-(6-bromo-4,5-dihydro-3H-1,3-benzodiazepin-2-yl)-6-methyl-morpholin-4-yl]quinoline-8-carbonitrile (Example 14)

To a 5 mL microwave vial was added (2R,6R)—N-(2-amino-6-bromophenethyl)-4-(8-cyanoquinolin-5-yl)-6-methylmorpholine-2-carboxamide (compound 14e, 110 mg, 0.22 mmol) and T$_3$P (1 ml, propylphosphonic anhydride solution, 50 wt. % in ethyl acetate). After the reaction mixture was heated in the microwave reactor at 100° C. for 30 min, it was concentrated and the residue was diluted with sat. NaHCO$_3$ (20 mL) and extracted with EtOAc (20 mL) twice. The combined organic layer was washed with brine, dried over Na$_2$SO$_4$, filtered and concentrated in vacuo. The residue was purified by silica gel column chromatography (eluted with PE:EtOAc=3:1 to 1:7) to afford Example 14 (70 mg, 66% yield) as a yellow solid. MS: calc'd 476 and 478 [(M+H)$^+$], measured 476 and 478 [(M+H)$^+$]. $^1$H NMR (400 MHz, METHANOL-d$_4$) δ ppm 9.02 (dd, J=4.22, 1.65 Hz, 1H), 8.79 (dd, J=8.62, 1.53 Hz, 1H), 8.18 (d, J=7.95 Hz, 1H), 7.70 (dd, J=8.56, 4.28 Hz, 1H), 7.32 (d, J=8.07 Hz, 1H), 7.27 (d, J=7.58 Hz, 1H), 6.95-7.10 (m, 2H), 4.64 (br d, J=7.83 Hz, 1H), 4.18-4.29 (m, 1H), 3.76-3.81 (m, 1H), 3.48-3.74 (m, 3H), 3.44-3.47 (m, 1H), 3.18-3.29 (m, 1H), 2.87-3.02 (m, 1H), 2.73-2.87 (m, 1H), 1.39 (d, J=6.36 Hz, 3H).

Example 15

5-[(2R,6R)-2-(4,5-dihydro-3H-1,3-benzodiazepin-2-yl)-6-methyl-morpholin-4-yl]quinoline-8-carbonitrile

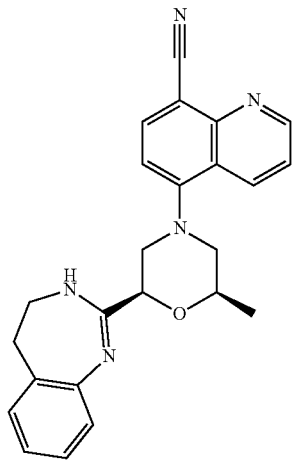 [SMILES: C[C@@H]1CN(c2ccc(C#N)c3ncccc23)C[C@H](C2=Nc3ccccc3CCN2)O1]

The title compound was prepared according to the scheme below:

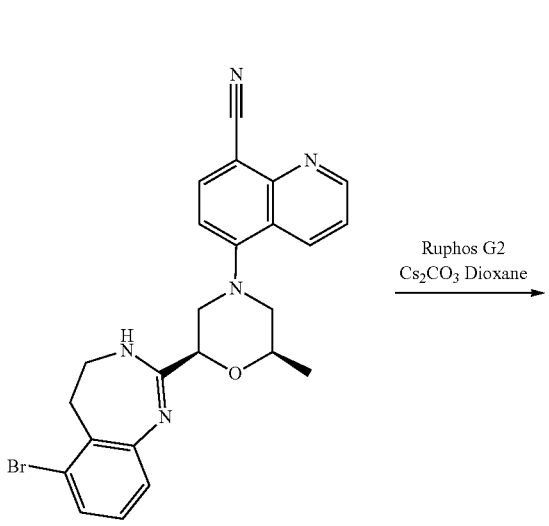

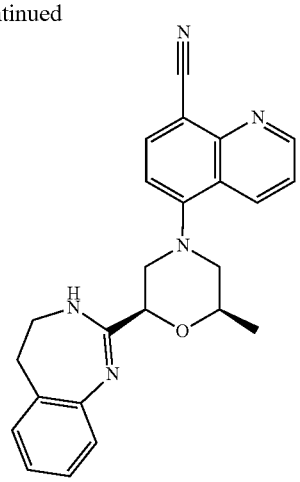

15

A mixture of 5-[(2R,6R)-2-(6-bromo-4,5-dihydro-3H-1,3-benzodiazepin-2-yl)-6-methyl-morpholin-4-yl]quinoline-8-carbonitrile (Example 14, 30 mg, 0.063 mmol), RuPhos G2 (4.6 mg, 0.006 mmol) and $Cs_2CO_3$ (61 mg, 0.19 mmol) in dioxane (5 mL) was charged with $N_2$, and stirred at 80° C. overnight. After cooled to rt, the reaction mixture was filtered through Celite and the filter cake was washed with EA (10 mL) twice, and the combined filtrate was concentrated in vacuo. The residue was purified by prep-HPLC to afford Example 15 (4.5 mg, 18% yield) as a yellow solid. MS: calc'd 398 [(M+H)$^+$], measured 398 [(M+H)$^+$]. $^1$H NMR (400 MHz, METHANOL-d$_4$) δ ppm 9.04 (dd, J=4.22, 1.53 Hz, 1H), 8.78 (dd, J=8.62, 1.53 Hz, 1H), 8.21 (d, J=7.95 Hz, 1H), 7.73 (dd, J=8.56, 4.28 Hz, 1H), 7.39 (d, J=8.07 Hz, 1H), 7.24-7.36 (m, 4H), 5.01 (dd, J=10.39, 2.45 Hz, 1H), 4.35-4.39 (m, 1H), 3.81-3.91 (m, 2H), 3.72-3.81 (m, 1H), 3.53 (br d, J=12.35 Hz, 1H), 3.25-3.29 (m, 2H), 3.17 (t, J=11.13 Hz, 1H), 2.84 (dd, J=12.23, 10.39 Hz, 1H), 1.43 (d, J=6.24 Hz, 3H).

Example 16

5-[(2R,6R)-2-methyl-6-[6-(1,2,3,6-tetrahydropyridin-4-yl)-4,5-dihydro-3H-1,3-benzodiazepin-2-yl]morpholin-4-yl]quinoline-8-carbonitrile

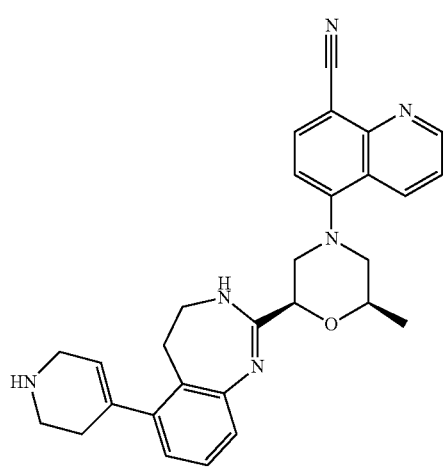 [SMILES: C[C@@H]1CN(c2ccc(C#N)c3ncccc23)C[C@H](C2=Nc3cccc(C4=CCNCC4)c3CCN2)O1]

The title compound was prepared according to the scheme below:

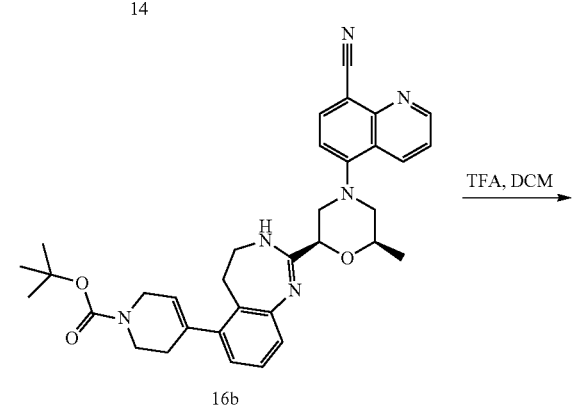

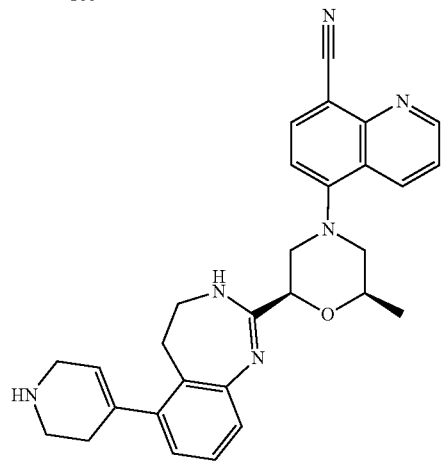

Step 1: Preparation of tert-butyl 4-[2-[(2R,6R)-4-(8-cyano-5-quinolyl)-6-methyl-morpholin-2-yl]-4,5-dihydro-3H-1,3-benzodiazepin-6-yl]-3,6-dihydro-2H-pyridine-1-carboxylate (16b)

To a solution 5-[(2R,6R)-2-(6-bromo-4,5-dihydro-3H-1,3-benzodiazepin-2-yl)-6-methyl-morpholin-4-yl]quinoline-8-carbonitrile (Example 14, 30 mg, 0.06 mmol) in 1,4-dioxane (5 mL) was added tert-butyl 4-(4,4,5,5-tetramethyl-1,3,2-dioxaborolan-2-yl)-3,6-dihydro-2H-pyridine-1-carboxylate (compound 16a, 55.6 mg, 0.18 mmol), $K_2CO_3$ (2 M, 0.09 mL, 0.18 mmol) and Pd(dppf)Cl$_2$.DCM (5 mg, 0.006 mmol), and the mixture was stirred at 100° C. for 2 hrs under N$_2$. The reaction mixture was concentrated in vacuo and the residue was purified by silica gel column chromatography (eluted with PE:EtOAc=3:1 to 1:2) to afford compound 16b (19 mg, 54% yield) as a yellow solid. MS: calc'd 579 [(M+H)$^+$], measured 579 [(M+H)$^+$].

Step 2: Preparation of 5-[(2R,6R)-2-methyl-6-[6-(1,2,3,6-tetrahydropyridin-4-yl)-4,5-dihydro-3H-1,3-benzodiazepin-2-yl]morpholin-4-yl]quinoline-8-carbonitrile (Example 16)

To a solution of tert-butyl 4-[2-[(2R,6R)-4-(8-cyano-5-quinolyl)-6-methyl-morpholin-2-yl]-4,5-dihydro-3H-1,3-benzodiazepin-6-yl]-3,6-dihydro-2H-pyridine-1-carboxylate (compound 16b, 19 mg, 0.033 mmol) in DCM (3 mL) was added TFA (1 mL) dropwise at 0° C. The reaction mixture was stirred at rt for 1 hr, then concentrated to give a crude product which was purified by prep-HPLC to afford Example 16 (13 mg, 82% yield) as a yellow solid. MS: calc'd 479 [(M+H)$^+$], measured 479 [(M+H)$^+$]. $^1$H NMR (400 MHz, METHANOL-d$_4$) δ ppm 9.05 (dd, J=4.28, 1.59 Hz, 1H), 8.78 (dd, J=8.56, 1.59 Hz, 1H), 8.21 (d, J=8.07 Hz, 1H), 7.73 (dd, J=8.68, 4.28 Hz, 1H), 7.33-7.43 (m, 2H), 7.27-7.32 (m, 1H), 7.18 (dd, J=7.52, 1.16 Hz, 1H), 5.70 (br s, 1H), 5.06 (dd, J=10.52, 2.57 Hz, 1H), 4.30-4.45 (m, 1H), 3.70-3.91 (m, 5H), 3.45-3.63 (m, 3H), 3.31-3.34 (m, 2H), 3.13-3.23 (m, 1H), 2.85 (dd, J=12.17, 10.45 Hz, 1H), 2.59 (br d, J=1.96 Hz, 2H), 1.43 (d, J=6.24 Hz, 3H).

Example 17

5-[(2R,6R)-2-methyl-6-(7-piperazin-1-yl-4,5-dihydro-3H-1,3-benzodiazepin-2-yl)morpholin-4-yl]quinoline-8-carbonitrile

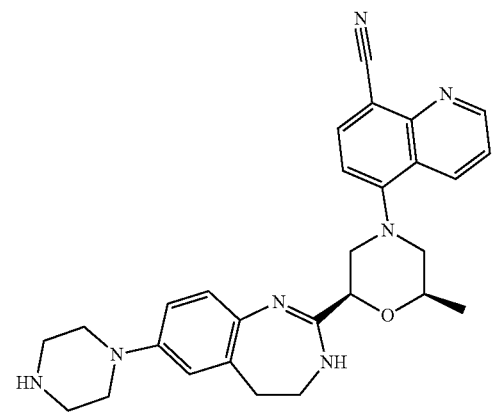 [SMILES: C[C@@H]1CN(c2ccc(C#N)c3ncccc23)C[C@H](C2=Nc3ccc(N4CCNCC4)cc3CCN2)O1]

The title compound was prepared according to the scheme below:

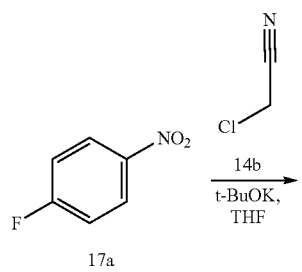

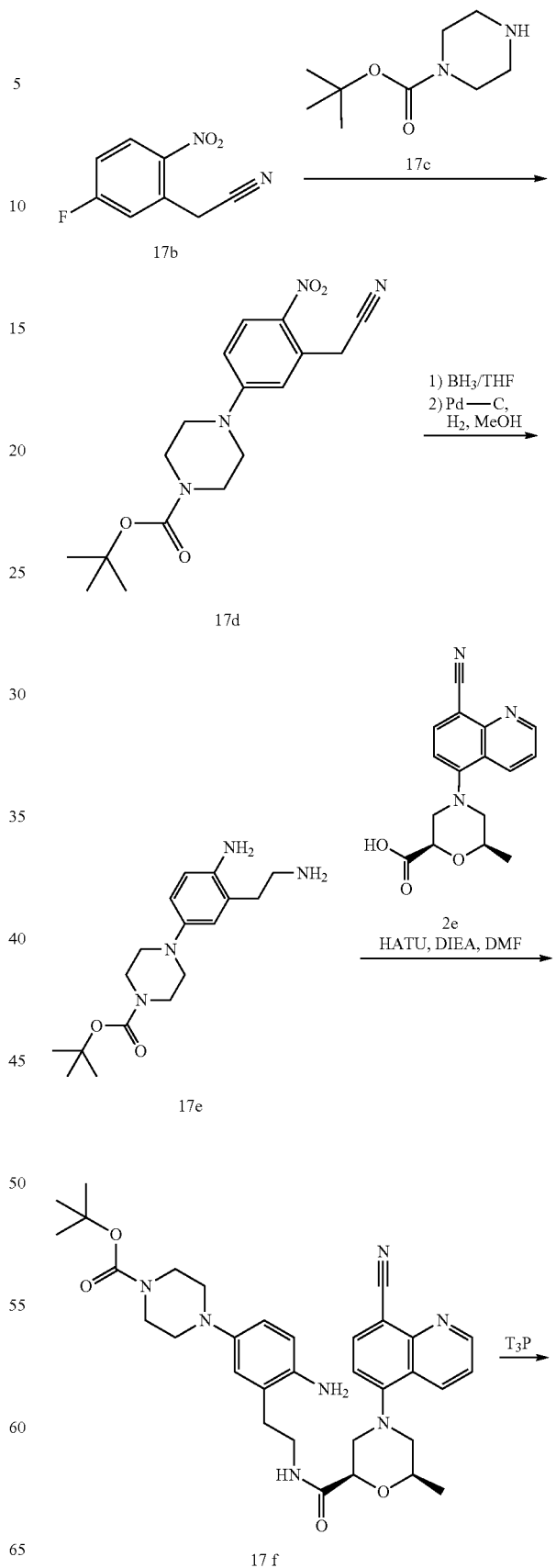

-continued

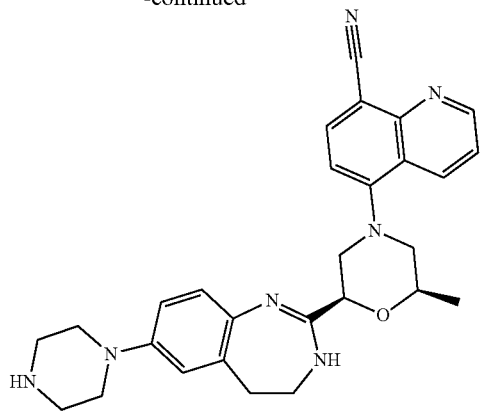

17 p 1: Preparation of 2-(5-fluoro-2-nitro-phenyl)acetonitrile (Compound 17b)

To a cooled solution of potassium tert-butoxide (3.2 g, 28.4 mmol) in THF (20 ml), a solution of 2-chloroacetonitrile (compound 14b, 1.0 g, 14.2 mmol) and 1-fluoro-4-nitrobenzene (compound 17a, 2.0 g, 14.2 mmol) in THF (20 ml) was added within 10 mins. During the addition the reaction temperature was kept at −10° C. to −20° C. About 10 mins after the addition was completed, the mixture was acidified with HCl (1 N) to pH around 5, and extracted with DCM (100 mL) twice. The combined organic layer was washed with water and brine, dried over $Na_2SO_4$, filtered, and concentrated in vacuo. The residue was purified by silica gel column chromatography (eluted with PE:EtOAc=20:1 to 4:1) to afford compound 17b (820 mg, 32% yield) as a yellow solid. MS: calc'd 179 [(M−H)⁻], measured 179 [(M−H)⁻].

Step 2: Preparation of tert-butyl 4-[3-(cyanomethyl)-4-nitro-phenyl]piperazine-1-carboxylate (Compound 17d)

The mixture of 2-(5-fluoro-2-nitrophenyl)acetonitrile (compound 17b, 500 mg, 2.8 mmol) and tert-butyl piperazine-1-carboxylate (compound 17c, 1.5 g, 8.3 mmol) was heated at 100° C. for 2 hrs, then diluted with $H_2O$ (50 ml) and extracted with EtOAc (50 mL) twice. The combined organic layer was washed with brine (20 mL) twice, dried over $Na_2SO_4$, filtered and concentrated in vacuo. The residue was purified by silica gel flash chromatography (eluted with DCM:EtOAc=10:1 to 1:2) to afford compound 17d (820 mg, 84% yield) as a yellow solid. MS: calc'd 345 [(M−H)⁻], measured 345 [(M−H)⁻].

Step 3: Preparation of tert-butyl 4-[4-amino-3-(2-aminoethyl)phenyl]piperazine-1-carboxylate (Compound 17e)

A mixture of tert-butyl 4-[3-(cyanomethyl)-4-nitro-phenyl]piperazine-1-carboxylate (compound 17d, 500 mg, 1.4 mmol) and $BH_3$ (1 M in THF, 20 mL, 20 mmol) was heated to reflux for 3 hrs. After cooled to rt, the mixture was quenched by addition of MeOH (5 mL) dropwise and the solvents were removed in vacuo. The residue was dissolved in EtOAc (50 mL) and washed with aqueous NaOH (0.5 N, 20 mL). The organic layer was dried over anhydrous $Na_2SO_4$, filtered and concentrated in vacuo. To the resultant yellow oil was added MeOH (20 mL), THF (15 mL) and $Pd(OH)_2$ (100 mg). Then the reaction mixture was stirred under hydrogen gas atmosphere (1 atm) at rt for 3 hrs. After the catalyst was filtered off, the filtrate was concentrated in vacuo to afford compound 17e (330 mg, 73% yield) as a brown oil which was used directly for the next step without further purification. MS: calc'd 321 [(M+H)⁺], measured 321 [(M+H)⁺].

Step 4: Preparation of tert-butyl 4-[4-amino-3-[2-[[(2R,6R)-4-(8-cyano-5-quinolyl)-6-methyl-morpholine-2-carbonyl]amino]ethyl]phenyl]piperazine-1-carboxylate (Compound 17f)

To a solution of (2R,6R)-4-(8-cyanoquinolin-5-yl)-6-methylmorpholine-2-carboxylic acid (compound 2e, 35 mg, 0.12 mmol) in DMF (5 mL) was added tert-butyl 4-(4-amino-3-(2-aminoethyl)phenyl)piperazine-1-carboxylate (compound 17e, 37.7 mg, 0.12 mmol), HATU (44.8 mg, 0.12 mmol) and TEA (59.6 mg, 0.59 mmol). The reaction mixture was stirred at rt for 30 mins, then poured into 10 mL $H_2O$ and extracted with EtOAc (25 mL) twice. The combined organic layer was washed with brine (10 mL) twice, dried over $Na_2SO_4$, filtered and the filtrate was concentrated in vacuo. The residue was purified by silica gel column chromatography (eluted with PE:EtOAc=1:1 to 0:1) to afford compound 17f (31 mg, 43% yield) as a yellow oil. MS: calc'd 600 [(M+H)⁺], measured 600 [(M+H)⁺].

Step 5: Preparation of 5-[(2R,6R)-2-methyl-6-(7-piperazin-1-yl-4,5-dihydro-3H-1,3-benzodiazepin-2-yl)morpholin-4-yl]quinoline-8-carbonitrile (Example 17)

To a 5 mL microwave vial was added 4-[4-amino-3-[2-[[(2R,6R)-4-(8-cyano-5-quinolyl)-6-methyl-morpholine-2-carbonyl]amino]ethyl]phenyl]piperazine-1-carboxylate (compound 17f, 16 mg, 0.027 mmol) and $T_3P$ (1 mL, propylphosphonic anhydride solution, 50 wt. % in ethyl acetate). The vial was capped and heated in the microwave at 100° C. for 30 mins. The reaction mixture was concentrated, and then diluted with $NaHCO_3$ (sat, 20 mL), extracted with EtOAc (20 mL) twice. The combined organic layer was washed with brine, dried over $Na_2SO_4$, filtered and concentrated in vacuo. The residue was purified by prep-HPLC to afford Example 17 (3.2 mg, 24% yield) as a yellow solid. MS: calc'd 482 [(M+H)⁺], measured 482 [(M+H)⁺]. ¹H NMR (400 MHz, METHANOL-d₄) δ ppm 8.93 (dd, J=4.28, 1.59 Hz, 1H), 8.65 (dd, J=8.68, 1.59 Hz, 1H), 8.09 (d, J=7.95 Hz, 1H), 7.60 (dd, J=8.56, 4.28 Hz, 1H), 7.26 (d, J=8.07 Hz, 1H), 7.14 (d, J=8.80 Hz, 1H), 6.90 (dd, J=8.86, 2.75 Hz, 1H), 6.85 (d, J=2.81 Hz, 1H), 4.89 (dd, J=10.39, 2.45 Hz, 1H), 4.18-4.32 (m, 1H), 3.68-3.78 (m, 2H), 3.63 (br d, J=11.74 Hz, 1H), 3.38-3.46 (m, 1H), 3.32-3.38 (m, 4H), 3.23-3.31 (m, 4H), 3.13 (br d, J=1.96 Hz, 2H), 3.02-3.09 (m, 1H), 2.72 (dd, J=12.29, 10.45 Hz, 1H), 1.30 (d, J=6.24 Hz, 3H).

Example 18

5-[(2R,6R)-2-methyl-6-[5-(4-piperidyl)-3,4-dihydro-quinazolin-2-yl]morpholin-4-yl]quinoline-8-carbonitrile

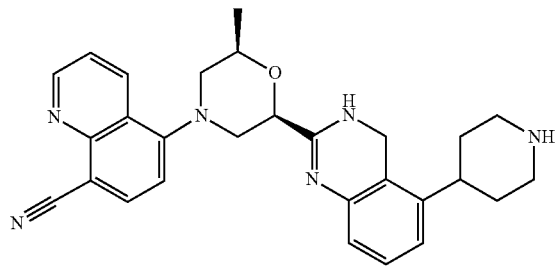 [SMILES: C[C@@H]1CN(c2ccc(C#N)c3ncccc23)C[C@H](C2=Nc3cccc(C4CCNCC4)c3CN2)O1]

The title compound was prepared in analogy to the preparation of Example 6 by using tert-butyl 4-(2-cyano-3-nitro-phenyl)-3,6-dihydro-2H-pyridine-1-carboxylate (compound 18b) instead of tert-butyl 4-(2-cyano-3-nitrophenyl) piperazine-1-carboxylate (compound 6c). Example 18 (19 mg) was obtained as a light brown solid. MS: calc'd 467 [(M+H)$^+$], measured 467 [(M+H)$^+$]. $^1$H NMR (400 MHz, METHANOL-d$_4$) δ=9.34 (br d, J=7.58 Hz, 1H), 9.21 (br d, J=3.79 Hz, 1H), 8.42 (br d, J=7.09 Hz, 1H), 8.09 (br s, 1H), 7.60 (br d, J=7.21 Hz, 1H), 7.31-7.40 (m, 1H), 7.26 (d, J=7.70 Hz, 1H), 7.12 (d, J=7.70 Hz, 1H), 5.19 (br d, J=7.70 Hz, 1H), 4.85 (br d, J=4.89 Hz, 2H), 4.34 (br s, 1H), 3.96 (br d, J=7.34 Hz, 1H), 3.45-3.65 (m, 3H), 3.25 (br s, 3H), 2.89-3.09 (m, 2H), 1.88-2.14 (m, 4H), 1.45 (br d, J=5.38 Hz, 3H).

Preparation of tert-butyl 4-(2-cyano-3-nitro-phenyl)-3,6-dihydro-2H-pyridine-1-carboxylate (Compound 18b)

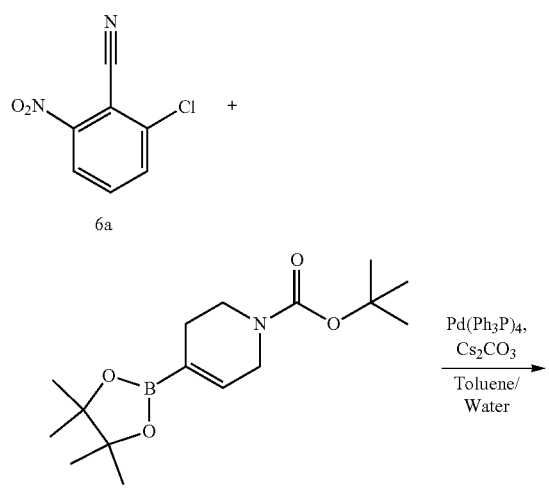

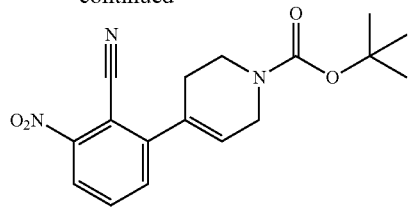

A mixture of 2-chloro-6-nitrobenzonitrile (compound 6a, 70.8 mg, 0.39 mmol), tert-butyl 4-(4,4,5,5-tetramethyl-1,3,2-dioxaborolan-2-yl)-3,6-dihydropyridine-1(2H)-carboxylate (compound 18a, CAS: 286961-14-6, Shaoyuan, 100 mg, 0.32 mmol), Cs$_2$CO$_3$ (158 mg, 0.48 mmol), and Pd(Ph$_3$P)$_4$ (18.7 mg, 0.016 mmol) in toluene (5 mL) and water (1 mL) was charged with N$_2$ and heated to 80° C. overnight. After cooled to rt, the reaction mixture was diluted with EtOAc (20 mL) and washed with water (10 mL). The organic layer was dried over Na$_2$SO$_4$, filtered and concentrated in vacuo. The residue was purified by silica gel column chromatography (eluted with PE:EtOAc=10:1 to 1:1) to give compound 18b (78 mg, 73%) as a light yellow solid. MS: calc'd 330 [(M+H)$^+$], measured 330 [(M+H)$^+$].

Example 19

The following tests were carried out in order to determine the activity of the compounds of formula (I) in HEK293-Blue-hTLR-7/8/9 cells assay.

HEK293-Blue-hTLR-7 Cells Assay:

A stable HEK293-Blue-hTLR-7 cell line was purchased from InvivoGen (Cat. #: hkb-htlr7, San Diego, Calif., USA). These cells were originally designed for studying the stimulation of human TLR7 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR7 cells with TLR7 ligands. Therefore the reporter expression was declined by TLR7 antagonist under the stimulation of a ligand, such as R848 (Resiquimod), for incubation of 20 h. The cell culture supernatant SEAP reporter activity was determined using QUANTI-Blue™ kit (Cat. #: rep-qb1, Invivogen, San Diego, Calif., USA) at a wavelength of 640 nm, a detection medium that turns purple or blue in the presence of alkaline phosphatase.

HEK293-Blue-hTLR7 cells were incubated at a density of 250,000~450,000 cells/mL in a volume of 170 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum with addition of 20 μL test compound in a serial dilution in the presence of final DMSO at 1% and 10 μL of 20 uM R848 in above DMEM, perform incubation under 37° C. in a CO$_2$ incubator for 20 h. Then 20 μL of the supernatant from each well was incubated with 180 μL Quanti-blue substrate solution at 37° C. for 2 h and the absorbance was read at 620-655 nm using a spectrophotometer. The signalling pathway that TLR7 activation leads to downstream NF-κB activation has been widely accepted, and therefore similar reporter assay was modified for evaluating TLR7 antagonist.

HEK293-Blue-hTLR-8 Cells Assay:

A stable HEK293-Blue-hTLR-8 cell line was purchased from InvivoGen (Cat. #: hkb-htlr8, San Diego, Calif., USA). These cells were originally designed for studying the stimulation of human TLR8 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR8 cells with TLR8 ligands. Therefore the reporter expression was declined by TLR8 antagonist under the stimulation of a ligand, such as R848, for incubation of 20 h. The cell culture supernatant SEAP reporter activity was determined using QUANTI-Blue™ kit (Cat. #: rep-qb1, Invivogen, San Diego, Calif., USA) at a wavelength of 640 nm, a detection medium that turns purple or blue in the presence of alkaline phosphatase.

HEK293-Blue-hTLR8 cells were incubated at a density of 250,000~450,000 cells/mL in a volume of 170 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum with addition of 20 μL test compound in a serial dilution in the presence of final DMSO at 1% and 10 μL of 60 uM R848 in above DMEM, perform incubation under 37° C. in a $CO_2$ incubator for 20 h. Then 20 μL of the supernatant from each well was incubated with 180 μL Quanti-blue substrate solution at 37° C. for 2 h and the absorbance was read at 620~655 nm using a spectrophotometer. The signalling pathway that TLR8 activation leads to downstream NF-κB activation has been widely accepted, and therefore similar reporter assay was modified for evaluating TLR8 antagonist.

HEK293-Blue-hTLR-9 Cells Assay:

A stable HEK293-Blue-hTLR-9 cell line was purchased from InvivoGen (Cat. #: hkb-htlr9, San Diego, Calif., USA). These cells were originally designed for studying the stimulation of human TLR9 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR9 cells with TLR9 ligands. Therefore the reporter expression was declined by TLR9 antagonist under the stimulation of a ligand, such as ODN2006 (Cat. #: tlrl-2006-1, Invivogen, San Diego, Calif., USA), for incubation of 20 h. The cell culture supernatant SEAP reporter activity was determined using QUANTI-Blue™ kit (Cat. #: rep-qb1, Invivogen, San Diego, Calif., USA) at a wavelength of 640 nm, a detection medium that turns purple or blue in the presence of alkaline phosphatase.

HEK293-Blue-hTLR9 cells were incubated at a density of 250,000~450,000 cells/mL in a volume of 170 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum with addition of 20 μL test compound in a serial dilution in the presence of final DMSO at 1% and 10 μL of 20 uM ODN2006 in above DMEM, perform incubation under 37° C. in a $CO_2$ incubator for 20 h. Then 20 μL of the supernatant from each well was incubated with 180 μL Quanti-blue substrate solution at 37° C. for 2 h and the absorbance was read at 620~655 nm using a spectrophotometer. The signalling pathway that TLR9 activation leads to downstream NF-κB activation has been widely accepted, and therefore similar reporter assay was modified for evaluating TLR9 antagonist.

The compounds of formula (I) have human TLR7 and/or TLR8 inhibitory activities ($IC_{50}$ value) <0.5 μM, particularly <0.050 μM. Moreover, some compounds of this invention also have human TLR9 inhibitory activity <0.5 μM, particularly <0.1 μM. Activity data of the compounds of the present invention were shown in Table 1.

TABLE 1

The activity of the compounds of present invention in HEK293-Blue-hTLR-7/8/9 cells assays

| Example | TLR7 $IC_{50}$ (μM) | TLR8 $IC_{50}$ (μM) | TLR9 $IC_{50}$ (μM) |
|---|---|---|---|
| 6 | 0.040 | 0.008 | 0.050 |
| 7 | 0.012 | <0.003 | 0.102 |
| 8 | 0.018 | 0.004 | 0.065 |
| 9 | 0.036 | 0.046 | 0.097 |
| 12 | 0.083 | 0.014 | 0.042 |
| 13 | 0.294 | 0.087 | 0.313 |
| 16 | 0.251 | 0.191 | 0.064 |
| 17 | 0.362 | 0.148 | 0.049 |
| 18 | 0.130 | 0.071 | 0.090 |

The invention claimed is:

1. A compound of formula (I),

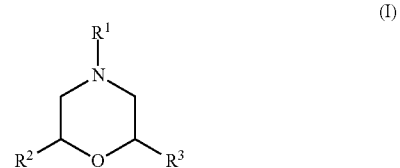

wherein:
$R^1$ is

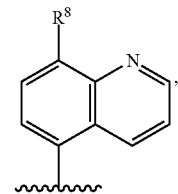

wherein $R^8$ is cyano, $C_{1-6}$alkyl, halogen, halo$C_{1-6}$alkyl or nitro;
$R^2$ is $C_{1-6}$alkyl, $C_{3-7}$cycloalkyl or halo$C_{1-6}$alkyl; and
$R^3$ is

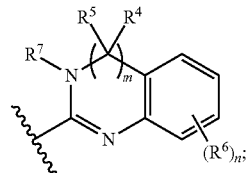

wherein:
$R^4$ and $R^5$ are independently selected from H and $C_{1-6}$alkyl;
$R^6$ is H, halogen, $C_{1-6}$alkyl or heterocyclyl;

$R^7$ is H or $C_{1-6}$alkyl;
m is 0, 1, 2 or 3; and
n is 1, 2 or 3;
or a pharmaceutically acceptable salt thereof.

2. A compound according to claim 1, wherein:
$R^1$ is

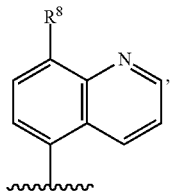

wherein $R^8$ is cyano;
$R^2$ is $C_{1-6}$alkyl; and
$R^3$ is

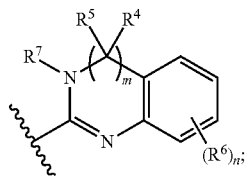

wherein:
$R^4$ is H;
$R^5$ is H;
$R^6$ is H, halogen, tetrahydropyridinyl, diazaspiro[4.4]nonanyl, hydroxypiperidinyl, $C_{1-6}$alkylpiperazinyl, morpholinyl, piperazinyl or piperidinyl;
$R^7$ is H; and
m is 1 or 2;
or a pharmaceutically acceptable salt thereof.

3. A compound according to claim 1, wherein:
$R^1$ is

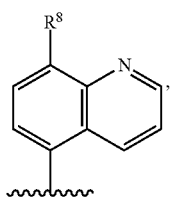

wherein $R^8$ is cyano;
$R^2$ is methyl;
$R^3$ is

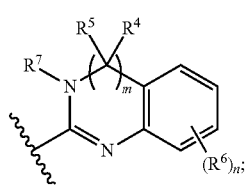

wherein:
$R^4$ is H;
$R^5$ is H;
$R^6$ is H, bromo, tetrahydropyridinyl, 2,7-diazaspiro[4.4]nonan-2-yl, hydroxypiperidinyl, methylpiperazinyl, morpholinyl, piperazinyl or piperidinyl;
$R^7$ is H; and
m is 1 or 2;
or a pharmaceutically acceptable salt thereof.

4. A compound according to claim 2, or pharmaceutically acceptable salt thereof, wherein $R^6$ is $C_{1-6}$alkylpiperazinyl or piperazinyl.

5. A compound according to claim 4, or pharmaceutically acceptable salt thereof, wherein $R^6$ is methylpiperazinyl or piperazinyl.

6. A compound according to claim 1, or pharmaceutically acceptable salt thereof, wherein n is 1.

7. A compound according to claim 2, selected from:
5-[(2R,6R)-2-(5-bromo-3,4-dihydroquinazolin-2-yl)-6-methyl-morpholin-4-yl]quinoline-8-carbonitrile;
5-[(2R,6R)-2-(6-bromo-3,4-dihydroquinazolin-2-yl)-6-methyl-morpholin-4-yl]quinoline-8-carbonitrile;
5-[(2R,6R)-2-(1,4-dihydroquinazolin-2-yl)-6-methyl-morpholin-4-yl]quinoline-8-carbonitrile;
5-[(2R,6R)-2-(7-bromo-3,4-dihydroquinazolin-2-yl)-6-methyl-morpholin-4-yl]quinoline-8-carbonitrile;
5-[(2R,6R)-2-(8-bromo-3,4-dihydroquinazolin-2-yl)-6-methyl-morpholin-4-yl]quinoline-8-carbonitrile;
5-[(2R,6R)-2-methyl-6-(5-piperazin-1-yl-3,4-dihydroquinazolin-2-yl)morpholin-4-yl]quinoline-8-carbonitrile;
5-[(2R,6R)-2-methyl-6-(6-piperazin-1-yl-3,4-dihydroquinazolin-2-yl)morpholin-4-yl]quinoline-8-carbonitrile;
5-[(2R,6R)-2-methyl-6-(7-piperazin-1-yl-3,4-dihydroquinazolin-2-yl)morpholin-4-yl]quinoline-8-carbonitrile;
5-[(2R,6R)-2-methyl-6-(8-piperazin-1-yl-3,4-dihydroquinazolin-2-yl)morpholin-4-yl]quinoline-8-carbonitrile;
5-[(2R,6R)-2-[5-(4-hydroxy-1-piperidyl)-3,4-dihydroquinazolin-2-yl]-6-methyl-morpholin-4-yl]quinoline-8-carbonitrile;
5-[(2R,6R)-2-methyl-6-(5-morpholino-3,4-dihydroquinazolin-2-yl)morpholin-4-yl]quinoline-8-carbonitrile;
5-[(2R,6R)-2-methyl-6-[5-(4-methylpiperazin-1-yl)-3,4-dihydroquinazolin-2-yl]morpholin-4-yl]quinoline-8-carbonitrile;
5-[(2R,6R)-2-[5-(2,7-diazaspiro[4.4]nonan-2-yl)-3,4-dihydroquinazolin-2-yl]-6-methyl-morpholin-4-yl]quinoline-8-carbonitrile;
5-[(2R,6R)-2-(6-bromo-4,5-dihydro-3H-1,3-benzodiazepin-2-yl)-6-methyl-morpholin-4-yl]quinoline-8-carbonitrile;
5-[(2R,6R)-2-methyl-6-[6-(1,2,3,6-tetrahydropyridin-4-yl)-4,5-dihydro-3H-1,3-benzodiazepin-2-yl]morpholin-4-yl]quinoline-8-carbonitrile;
5-[(2R,6R)-2-methyl-6-(7-piperazin-1-yl-4,5-dihydro-3H-1,3-benzodiazepin-2-yl)morpholin-4-yl]quinoline-8-carbonitrile; and
5-[(2R,6R)-2-methyl-6-[5-(4-piperidyl)-3,4-dihydroquinazolin-2-yl]morpholin-4-yl]quinoline-8-carbonitrile;
or a pharmaceutically acceptable salt thereof.

8. A process for preparing a compound according to claim 1, the process comprising:

a) cyclizing a compound of formula (VII)

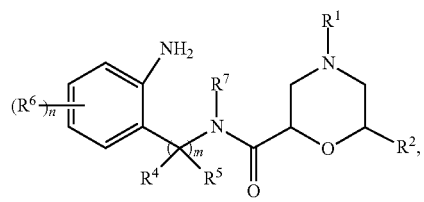

(VII)

in the presence of an acid;
wherein the acid is HCl in t-BuOH.

9. A pharmaceutical composition comprising a compound in accordance with claim 1, or a pharmaceutically acceptable salt thereof, and a therapeutically inert carrier.

10. A method for the treatment of systemic lupus erythematosus or lupus nephritis, which method comprises administering to a subject in need thereof a therapeutically effective amount of a compound as defined in claim 1, or a pharmaceutically acceptable salt thereof.

11. A method for the treatment of systemic lupus erythematosus or lupus nephritis, which method comprises administering to a subject in need thereof a therapeutically effective amount of a compound as defined in claim 7, or a pharmaceutically acceptable salt thereof.

12. A pharmaceutical composition comprising a compound in accordance with claim 7, or a pharmaceutically acceptable salt thereof, and a therapeutically inert carrier.

\* \* \* \* \*